United States Patent
Kato

(10) Patent No.: US 6,746,459 B2
(45) Date of Patent: Jun. 8, 2004

(54) END-TO-SIDE BLOOD VESSEL ANASTOMOSIS METHOD AND INSTRUMENTS THEREFOR

(75) Inventor: Yukitoshi Kato, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/977,276

(22) Filed: Oct. 16, 2001

(65) Prior Publication Data

US 2002/0049459 A1 Apr. 25, 2002

(30) Foreign Application Priority Data

Oct. 19, 2000 (JP) ............................ 2000-319788
Aug. 3, 2001 (JP) ............................ 2001-237088

(51) Int. Cl.$^7$ ............................................. A61B 17/04
(52) U.S. Cl. ............................................ 606/153; 606/140
(58) Field of Search ..................... 606/153, 213, 606/216, 217, 205, 207, 210, 211, 139, 140

(56) References Cited

U.S. PATENT DOCUMENTS

| | | | |
|---|---|---|---|
| 2,453,056 A | 11/1948 | Zack | |
| 4,041,931 A | 8/1977 | Elliott et al. | |
| 4,352,358 A | 10/1982 | Angelchik | |
| 4,366,819 A | 1/1983 | Kaster | |
| 4,368,736 A | 1/1983 | Kaster | |
| 4,607,637 A | 8/1986 | Berggren et al. | |
| 4,624,255 A | 11/1986 | Schenck et al. | |
| 4,657,019 A | 4/1987 | Walsh et al. | |
| 4,693,249 A | 9/1987 | Schenck et al. | |
| 4,787,386 A | 11/1988 | Walsh et al. | |
| 4,917,087 A | 4/1990 | Walsh et al. | |
| 4,931,057 A | 6/1990 | Cummings et al. | |
| 5,403,333 A | 4/1995 | Kaster et al. | |
| 5,425,738 A | 6/1995 | Gustafson et al. | |
| 5,503,635 A | 4/1996 | Sauer et al. | |
| 5,520,704 A * | 5/1996 | Castro et al. ............... | 606/208 |
| 5,707,380 A | 1/1998 | Hinchliffe et al. | |
| 5,725,544 A | 3/1998 | Rygaard | |
| 5,797,934 A | 8/1998 | Rygaard | |
| 5,833,698 A | 11/1998 | Hinchliffe et al. | |
| 5,868,770 A | 2/1999 | Rygaard | |
| 5,904,697 A | 5/1999 | Gifford, III et al. | |
| 5,954,735 A | 9/1999 | Rygaard | |
| 5,993,468 A | 11/1999 | Rygaard | |
| 6,024,748 A | 2/2000 | Manzo et al. | |
| 6,056,762 A | 5/2000 | Nash et al. | |
| 6,063,114 A | 5/2000 | Nash et al. | |
| 6,066,148 A | 5/2000 | Rygaard | |
| 6,074,416 A | 6/2000 | Berg et al. | |
| 6,190,397 B1 * | 2/2001 | Spence et al. ............... | 606/153 |
| 6,494,889 B1 * | 12/2002 | Fleischman et al. ........ | 606/155 |
| 6,517,554 B1 * | 2/2003 | Zhu et al. .................... | 606/150 |
| 2001/0001826 A1 * | 5/2001 | Bolduc et al. ............... | 606/153 |
| 2002/0173808 A1 * | 11/2002 | Houser et al. ............... | 606/153 |

FOREIGN PATENT DOCUMENTS

| | | |
|---|---|---|
| WO | 01/08601 A2 | 2/2001 |
| WO | WO 01/41624 A2 | 6/2001 |

* cited by examiner

Primary Examiner—Michael J. Milano
Assistant Examiner—Bradford C Pantuck
(74) Attorney, Agent, or Firm—Burns, Doane, Swecker & Mathis, L.L.P.

(57) ABSTRACT

A method of end-to-side anastomosis of blood vessels for connecting a side portion of a first blood vessel to an end portion of a second blood vessel involves holding a first site on the side portion of the first blood vessel using a holder, and partially elevating the side portion of the first blood vessel; superimposing a second site on the side portion of the first blood vessel on the end of the second blood vessel and fixing them with a ring-shaped fixing member to each other; and detaching the holder from the first blood vessel when they are fixed by the fixing member or after they are fixed. The end-to-side blood vessel anastomosis method can readily open the dissected portion on the side of the blood vessel upon end-to-side blood vessel anastomosis and retain it in that state. No foreign matter is present within the blood vessel after completion of the anastomosis.

15 Claims, 29 Drawing Sheets

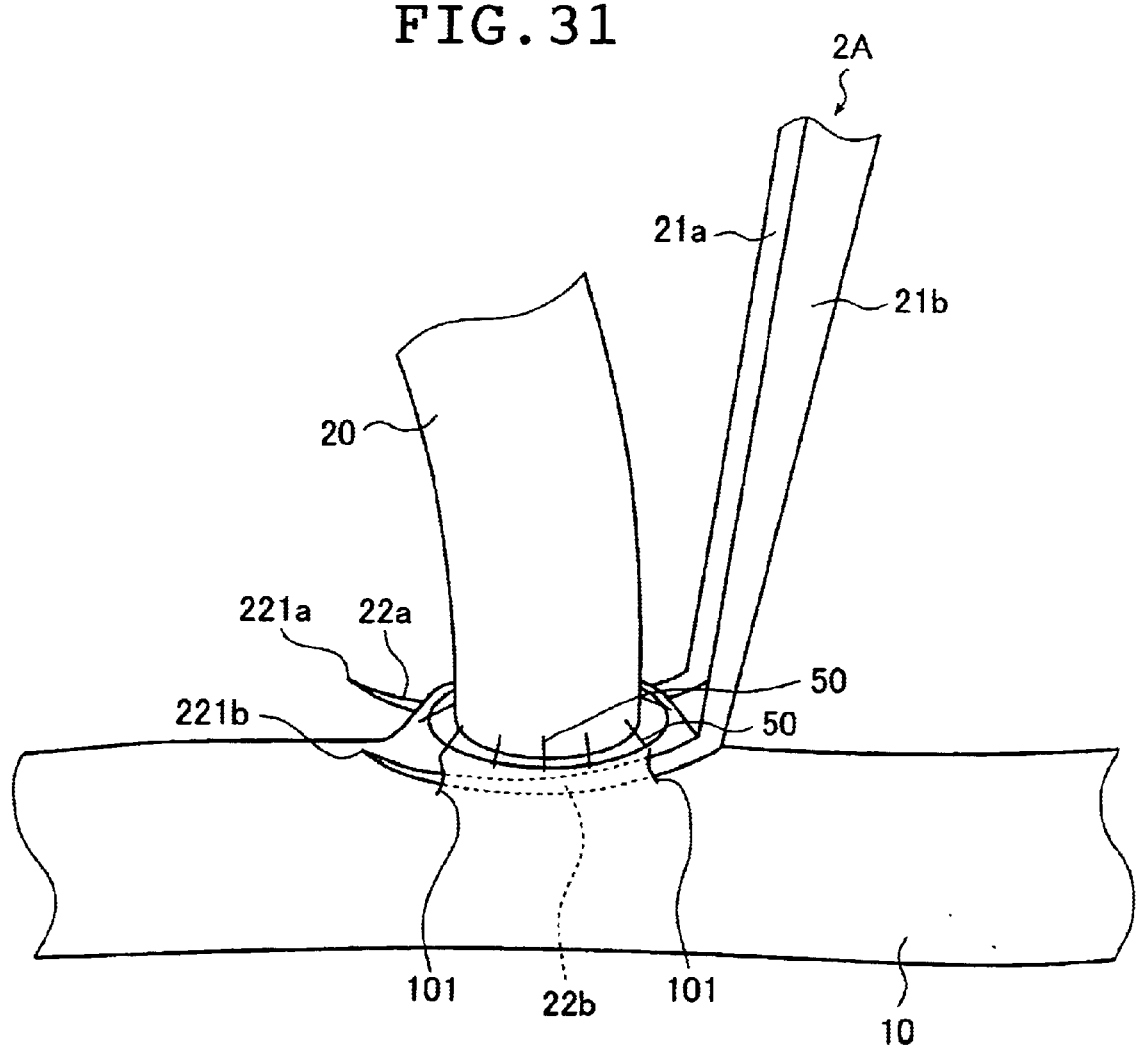

END-TO-SIDE BLOOD VESSEL ANASTOMOSIS METHOD AND INSTRUMENTS THEREFOR

BACKGROUND OF THE INVENTION

1. Field of the Invention

The present invention relates to a method of anastomosis of blood vessels, more particularly to a method of an end-to-side anastomosis of an end portion of one blood vessel to a side portion of another blood vessel and instruments used for this anastomosis method. Also, the present invention relates to a method of connection of a medical device constituting an extracorporeal circulation circuit, such as a pump-oxygenator, a dialyser for blood or body fluid, at a side portion of a blood vessel.

2. Description of the Related Art

In operations, an end-to-side anastomosis by connection of an end portion of a blood vessel with a side portion of another blood vessel to communicate the blood vessels with each other is sometimes carried out. For example, in coronary artery bypass graft (CABG) for the therapy of angina pectoris, cardiac infarction, arrythmia and so forth caused by insufficient circulation to the cardiac muscle due to the constriction of coronary artery, an end portion of internal thoracic artery or great saphenous vein, for example, is anastomosed (connected) to a side portion of coronary artery on its peripheral side with respect to the constricted site.

The end-to-side blood vessel anastomosis method is carried out usually by partially dissecting a side portion of one blood vessel to form an opening having a peripheral portion and suturing the peripheral portion with an end portion of another blood vessel with a needle and a suture. Such a technique requires a considerably high level skill. In particular, anastomosis of coronary artery bypass graft, which is carried out on blood vessels that are very thin and under a narrow field of vision, is very difficult to carry out.

In end-to-side anastomosis method for blood vessels, it is particularly important to maintain the opening formed on the side portion of one blood vessel to have a sufficient size for it to be anastomosed with the end portion of another blood vessel when the blood vessels are sutured with each other. In this respect, a conventional method as disclosed in U.S. Pat. No. 2,453,056 has been carried out as follows. That is, the peripheral portion of the opening attached to the side portion of a blood vessel is clipped with a plurality of tweezers to retain the opening at the side portion of the blood vessel in an expanded state sufficient for the end portion of another blood vessel to be anastomosed thereto and then the peripheral portion of the opening at the side portion of one blood vessel and the end portion of another blood vessel are connected to each other. However, the blood vessel of which anastomosis is needed usually is hardened and very brittle because of calcification or the like so that there is the fear that the blood vessel when clipped with tweezers or the like could be torn at the dissected portion.

Also, coronary artery bypass graft has been conventionally carried out in a cardiac arrest state using a pump-oxygenator. However, use of a pump-oxygenator gives much stress on patients. Accordingly, in recent years, low stress coronary artery bypass graft carried out in a state where the heart beats (under heart beating) (hereinafter referred to as "bypass graft under heart beating") has been carried out in order to alleviate load to the body of a patient, shorten the time required for curing and reduce medical expenses to be paid by the patient.

In the bypass graft under heart beating, the surface of the heart moves due to the heartbeat, which makes the blood vessel anastomosis more difficult.

In this regard, a method of connection between a peripheral portion of an opening at the side portion of one blood vessel and an end portion of another blood vessel by using a special instrument is disclosed in U.S. Pat. No. 4,787,386, for example. The special instrument has an annular shape provided with an opening in the center with a plurality of protrusions provided on an outer periphery of the annular portion. The protrusion of the instrument are pierced into the peripheral portion of the opening attached to the side portion of one blood vessel to retain the opening at the side portion of the blood vessel in an expanded state having a desired size. Then, the peripheral portion of the opening at the side portion of the blood vessel is connected to the end portion of another blood vessel.

However, in this connection method, it is necessary to retain the opening of a blood vessel in an expanded state with the tweezers or the like so as to have a sufficient size for the attachment of the instrument when the protrusions of the instrument thereto are pierced into the peripheral portion of the opening. This procedure itself is difficult as described above. Also, after the anastomosis, the protrusions of the instrument exist exposed in the passage of blood in the blood vessel. When they are in contact with the blood flow, they are recognized as foreign matter, leading to the possibility of thrombus formation.

SUMMARY OF THE INVENTION

An object of the present invention is to provide a method of end-to-side anastomosis of blood vessel that facilitates expansion of an opening provided on a side portion of a blood vessel to a desired size and enables retention of the opening in that state when a blood vessel is subjected to end-to-side anastomosis, and in which no foreign matter is present in the passage of blood in the blood vessel after completion of anastomosis.

Another object of the present invention is to provide an instrument for use in the method of end-to-side blood vessel anastomosis and more particularly to provide a blood vessel connecting instrument, a blood vessel supporting instrument or a surgical instrument.

Still another object of the present invention is to provide a method of connection of a medical device constituting an extracorporeal circulation circuit, such as a pump-oxygenator, a dialyser for blood or body fluid, with a side portion of a blood vessel.

The above objects have been achieved by the following items (1) to (34) according to the present invention.

(1) A method of end-to-side anastomosis of blood vessels for connecting a side portion of a first blood vessel to an end portion of a second blood vessel, comprising the steps of:

holding a first site on the side portion of the first blood vessel located in the vicinity of a peripheral portion of an opening formed on the side portion of the first blood vessel using a holder, and partially elevating the side portion of the first blood vessel;

superimposing a second site on the side portion of the first blood vessel that is more distant from the peripheral portion of the opening formed on the side portion of the first blood vessel than that from the first site and the end portion of the second blood vessel on each other and fixing them with a ring-shaped fixing member to each other; and detaching the holder from the first blood vessel when they are fixed using the fixing member or after they are fixed.

(2) A blood vessel connecting instrument for connecting to an opening formed on a side portion of a first blood vessel an end portion of a second blood vessel, comprising:
   at least one engaging member having an engaging portion for enabling engagement in the vicinity of a peripheral portion of an opening formed on the first blood vessel from inside thereof; and
   a holding means for holding the state of engagement of the engaging portion in the vicinity of the peripheral portion of the opening in the first blood vessel.

(3) A blood vessel connecting instrument according to the item (2) above, wherein the holding means is a holding member having a clipping portion that can clip a part of the first blood vessel in the vicinity of the opening in the first blood vessel between it and the engaging portion.

(4) A blood vessel connecting instrument according to the item (2) or (3) above, wherein the engaging member is arranged in the holding member movable in a longitudinal direction thereof.

(5) A blood vessel connecting instrument according to any one of the items (2) to (4) above, comprising a plurality of engaging members, at least two of which are variable with respect to the distance thereof.

(6) A blood vessel connecting instrument according to any one of the items (2) to (5) above, wherein the engaging member comprises a linear body and the engaging portion comprises a bent end portion of the linear body.

(7) A blood vessel connecting instrument according to any one of the items (2) to (6) above, further comprising a fastener member for superimposing a portion in the vicinity of the peripheral portion of the opening in the first blood vessel on the end portion of the second blood vessel and fastening them to fix them.

(8) A blood vessel connecting instrument according to the item (7) above, wherein the fastening member is ring-shaped and the diameter thereof is variable.

(9) A blood vessel connecting instrument according to the item (7) or (8) above, further comprising a guide portion for guiding the fastening member to a fixing position of the first blood vessel and the second blood vessel, and a moving means for moving the fastening member to the fixing position.

(10) A blood vessel connecting instrument according to the item (9) above, wherein the fixing portion is at a position remoter from the opening than the position at which the engaging portion is engaged with the inner surface of the first blood vessel.

(11) A blood vessel connecting instrument according to any one of the items (7) to (10) above, wherein the fastening member has a receiving member for receiving fastening force of the fastening member.

(12) A blood vessel connecting instrument according to the item (11) above, wherein the receiving member is ring-shaped.

(13) A blood vessel connecting instrument according to the item (11) or (12) above, wherein the receiving member has a groove on its outer periphery.

(14) A blood vessel connecting instrument according to any one of the items (11) to (13) above, further comprising a blood vessel supporting member for supporting the second blood vessel together with the receiving member.

(15) A blood vessel connecting instrument according to the item (14) above, wherein the blood vessel supporting member has a pair of arm portions that can come closer to and be spaced from each other.

(16) A blood vessel supporting instrument comprising:
   a pair of arm portions;
   a pair of needle portions attached to an end portion of the both arm portions, respectively and arranged substantially parallel to each other;
      wherein the needle portions are pierced into the blood vessel to support and manipulate a portion of the blood vessel.

(17) A blood vessel supporting instrument according to the item (16) above, wherein the needle portions has substantially circular or substantially ellipsoidal shape in a cross sectional view.

(18) A blood vessel supporting instrument according to the item (16) or (17) above, wherein the needle portions have each a length of 1.5 to 40.0 mm.

(19) A blood vessel according to any one of the items (16) to (18) above, wherein a distance between the both needle portions is variable.

(20) A blood vessel supporting instrument according to any one of the items (16) to (19) above, wherein the both needle portions are connected to each other in at least one position of a midway in the longitudinal direction thereof or the other end portion thereof.

(21) A blood vessel supporting instrument according to any one of the items (16) to (20) above, wherein the supporting instrument is capable of being fixed to a stabilizer for suppressing movement of heart surface.

(22) A blood vessel supporting instrument according to any one of the items (16) to (21) above, further comprising a dissection instrument attachment portion for detachably attaching a dissection instrument for dissecting the blood vessel.

(23) A blood vessel supporting instrument according to the item (22) above, wherein the dissection instrument is capable of being attached so that relative positional relation between a distal end portion of the dissecting instrument and the needle portions can be controlled.

(24) A surgical instrument comprising:
   a blood vessel supporting instrument according to any one of the items (16) to (23) above;
   a dissecting instrument attachable to the blood vessel supporting instrument;
      wherein a distal end portion of the dissecting instrument is movable with respect to the needle portions.

(25) A surgical instrument according to the item (24) above, wherein the instrument is capable of performing dissection in an appropriate length while controlling distance of movement of the distal end portion of the dissecting instrument with respect to the needle portions.

(26) A surgical instrument according to the item (24) or (25) above, wherein the distal end portion of the dissecting instrument is displaceable between a first position of being retracted from the blood vessel and a second position of dissecting the blood vessel.

(27) A surgical instrument according to any one of the items (24) to (26) above, further comprising a manipulating portion for manipulating movement of the distal end portion of the dissecting instrument to the needle portions.

(28) A surgical instrument according to any one of the items (24) to (27) above, wherein the dissecting instrument is one selected from the group consisting of a knife, a laser probe, an electric knife, and an ultrasonic knife.

(29) A method of end-to-side anastomosis of blood vessels according to the item (1), wherein the blood vessel connecting instrument according to the item (2) is utilized.

(30) A method of end-to-side anastomosis is of blood vessels according to the item (1), wherein the blood vessel supporting instrument according to the item (16) is utilized.

(31) A method of connection of a medical device constituting an extracorporeal blood circulation with a side portion of blood vessel, comprising the steps of:

holding a first site on the side portion of the blood vessel located in the vicinity of a peripheral portion of an opening formed on the side portion of the blood vessel using a holder, and partially elevating the side portion of the first blood vessel;

superimposing a second site on the side portion of the first blood vessel that locates more distant from the peripheral portion of the opening formed on the side portion of the first blood vessel than that of the first site therefrom is and a terminal end portion of a passage for blood of the medical device having a passage for blood wherein can connect with a blood vessel on each other and fixing them with a ring-shaped fixing member to each other; and detaching the holder from the blood vessel when they are fixed using the fixing member or after they are fixed.

(32) A method of connection of a medical device according to the item (31), wherein the blood vessel connecting instrument according to the blood vessel connecting instrument according to the item (2) is utilized.

(33) A method of connection of a medical device according to the item (31), wherein the blood vessel supporting instrument according to the item (16) is utilized.

BRIEF DESCRIPTION OF THE INVENTION

FIGS. 30 and 31 are schematic perspective views each showing the blood vessel supporting instrument, illustrating other modes of utilization thereof.

DESCRIPTION OF PREFERRED EMBODIMENTS OF THE INVENTION

Hereinafter, the end-to-side blood vessel anastomosis method and instrument used for this method according to preferred embodiments of the present invention will be illustrated in detail with reference to the attached drawings.

<First Embodiment>

Figure 7:
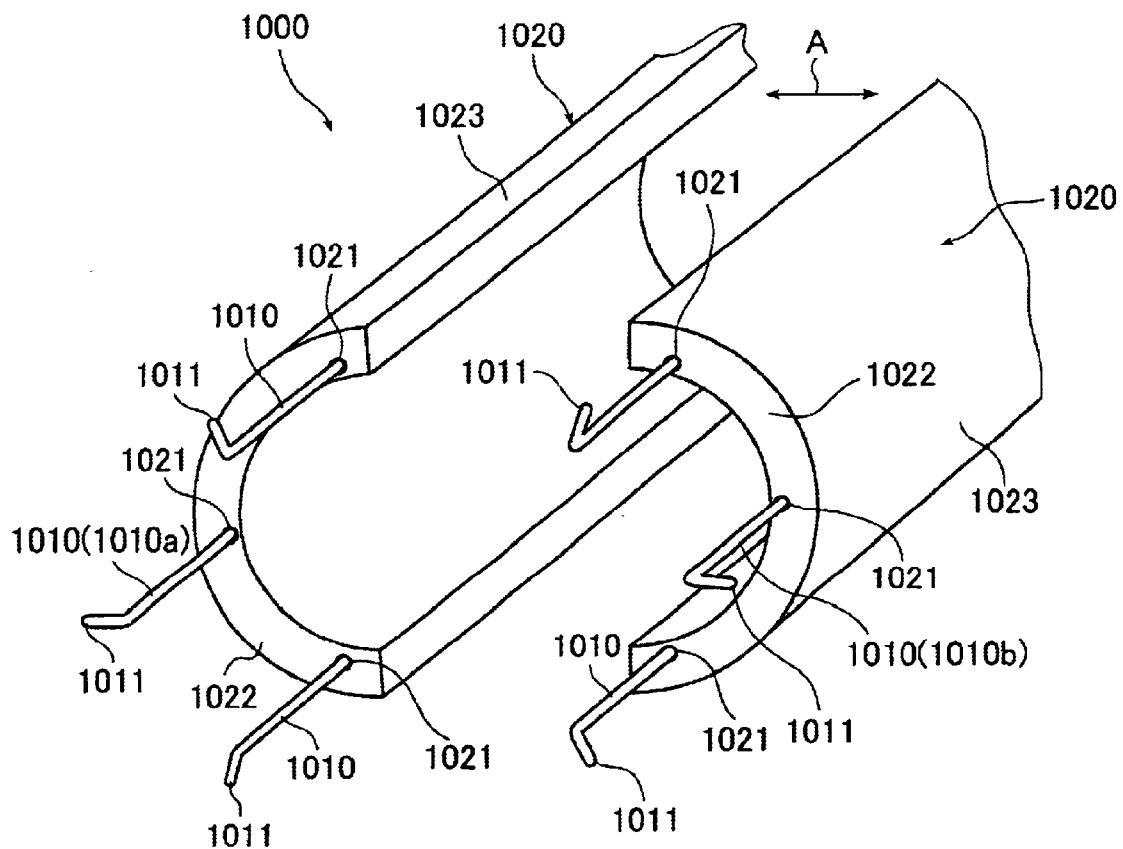
FIG. 7 is a perspective view showing a structure of a distal end portion of a blood vessel connecting instrument for use in an end-to-side blood vessel anastomosis method according to the first embodiment of the present invention.
Figure 8:
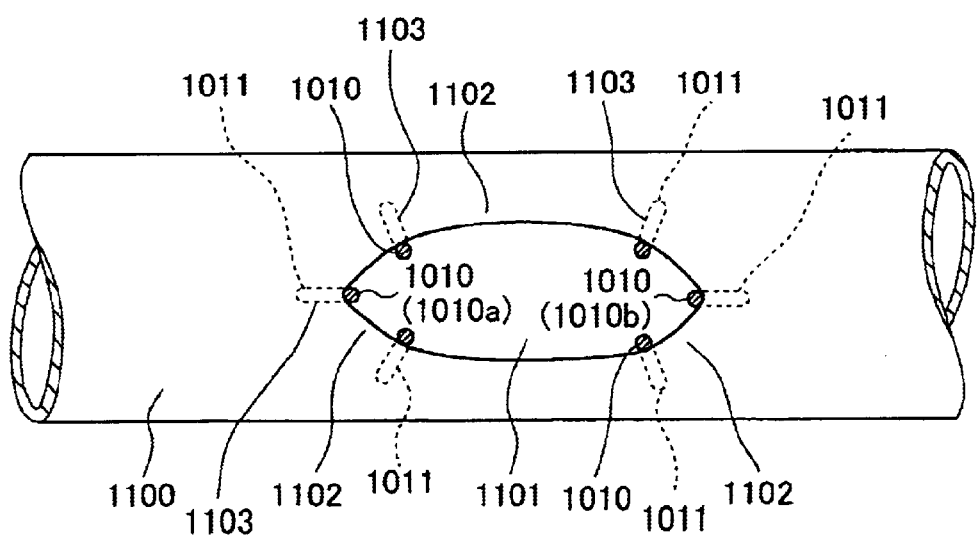
FIG. 8 is a plan view showing an engaging member of a blood vessel connecting instrument for use in an end-to-side blood vessel anastomosis method according to the first embodiment of the present invention, illustrating a state in which the engaging member is attached to an opening of a blood vessel.
Figure 9:
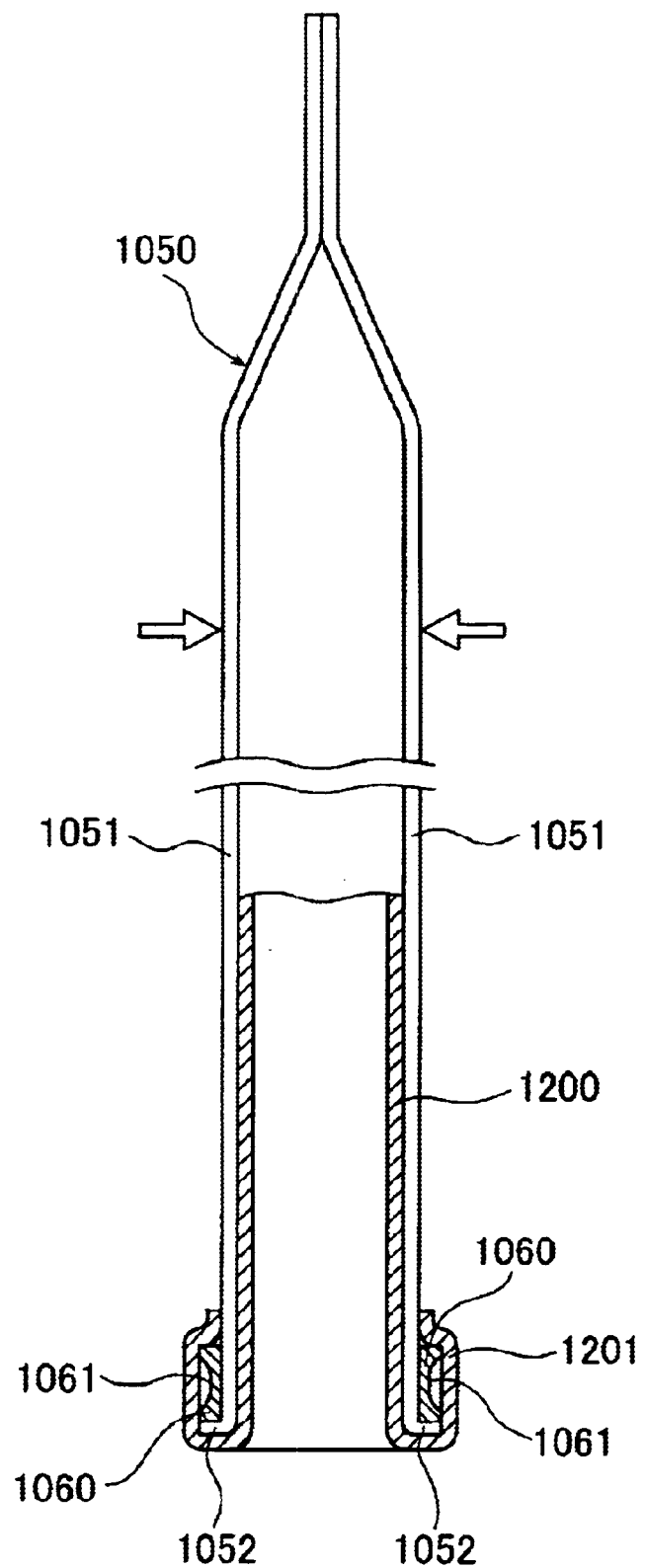
FIG. 9 is a partial sectional side view showing structures of a blood vessel supporting member and a receiving member in the blood vessel connecting instrument for use in an end-to-side blood vessel anastomosis method according to the first embodiment of the present invention.

FIGS. 1 to 6 are each a longitudinal cross sectional view showing a blood vessel connecting instrument for use in an end-to-side blood vessel anastomosis method according to a first embodiment of the present invention. FIG. 7 is a perspective view showing a structure of a distal end portion of a blood vessel connecting instrument for use in an end-to-side blood vessel anastomosis method according to a first embodiment of the present invention. FIG. 8 is a plan view showing an engaging member for use in an end-to-side blood vessel anastomosis method according to the first embodiment of the present invention, illustrating a state in which the engaging member is attached to an opening of a blood vessel. FIG. 9 is partial side view showing structures of a blood vessel supporting member and a receiving member in the blood vessel connecting instrument for use in an end-to-side blood vessel anastomosis method according to the first embodiment of the present invention. FIG. 10 is a perspective view showing a structure of a fastening member in the blood vessel connecting instrument for use in an end-to-side blood vessel anastomosis method according to the first embodiment of the present invention. In the following explanation, the upper side and lower side in FIGS. 1 to 6 and 10 are referred to as "proximal end" and "distal end", respectively.

A blood vessel connecting instrument 1000 in accordance with the present embodiment is a blood vessel connecting instrument for connecting an opening (i.e., opening formed by being dissected by means of a knife or the like) 1101 on a side portion of a first blood vessel 1100 and an end portion 1201 of a second blood vessel 1200 to each other. The connecting instrument 1000 is provided with a plurality of engaging members 1010, a pair of holding members 1020, a fastening member (fixing instrument) 1030, a pressing member 1040 for pressing and moving the fastening member (fixing instrument) 1030, a blood vessel supporting member 1050 for supporting the second blood vessel 1200, and a receiving member 1060 to be attached to the second blood vessel 1200. Hereinafter, the structure of each component is illustrated in detail.

As shown in FIG. 7, each holding member 1020 comprises a continuous member having a semi-circular cross section. Inside the each holding member 1020, three small holes 1021 extending in the longitudinal direction thereof are formed. In each small hole 1021, an engaging member 1010 constituted by a linear body is inserted.

The engaging member 1010 is movable in the longitudinal direction in the small hole 1021. The engaging member 1010 can also be rotated. This enables each engaging portion 1011 to assume a posture of being projected outwardly from a central portion of the opening 1101 (cf. FIGS. 7 and 8).

The distal end portion of the engaging member 1010 is projected from a top surface (clipping portion) 1022 of the holding member 1020. The distal end of the engaging member 1010 has an engaging portion (hook) 1011 formed by bending (folding) an end portion of the linear body substantially at right angles. The engaging portion 1011 can be engaged with a first site 1103 in the vicinity of an peripheral portion 1102 of the opening 1101 formed in the side portion of the first blood vessel 1100 from the inside.

As indicated by the arrow A in FIG. 7, the both holding members 1020 are movable in the direction in which they come closer to or remoter from each other. This makes it possible to vary the distance between the engaging members (three members) 1010 provided in the one holding member 1020 and the engaging members (three members) 1010 provided in the other holding member 1020. As a result of this, the engaging portions 1011 can be engaged under optimal conditions depending on the size, length (dissection length) and so forth of the opening 1101.

The blood vessel connecting instrument 1000 for use in the method of the present embodiment has in total six engaging members 1010. Two of them that are most spaced from each other, consist of an engaging member 1010a in the center of the three engaging members arranged in one holding member 1020 and an engaging member 1010b in the center of the three engaging members arranged in the other holding member 1020. The blood vessel connecting instrument 1000 is used such that an imaginary straight line connecting the engaging members 1010a and 1010b is directed in the longitudinal direction (in the direction of dissection) of the opening 1101 in the first blood vessel 1100. As a result of this the engaging portions 1011 can be engaged under optimal conditions depending on the size, length (dissection length) and so forth of the opening 1101.

The top surface 1022 of the holding member 1020 forms between it and the engaging portion 1011 a clipping portion that clips the first site 1103 in the vicinity of the peripheral portion 1102 of the opening 1101. That is, by relatively moving the engaging members 1010 in the direction toward the proximal end with respect to the holding member 1020, the first site 1103 positioned in the vicinity of the peripheral portion 1102 of the opening 1101 can be clipped between the engaging portion 1011 and the top surface 1022 of the holding member 1020. Thus, the holding member 1020 constitutes a holding means (holding instrument) for holding the state in which the engaging portion 1011 is engaged with the first site 1103 on the side portion of the first blood vessel 1100.

As a material for the holding member 1020, for example, various metal materials such as stainless steel, titanium or titanium alloys, and aluminum, and relatively hard resin materials such as polycarbonate, acrylic resin, polytetrafluoroethylene (Teflon resin), polyethylene, and polypropylene can be used.

Further, as the material for the engaging members 1010, for example, various metal materials such as stainless steel, superelastic alloys (Ni—Ti based alloys), and titanium or titanium alloys, and carbon fiber. Among these, superelastic alloys and titanium are particularly preferred in terms of excellent compatibility with blood vessels in organisms.

The wire diameter of the engaging member 1010 is not particularly limited. Usually, it is preferably about 0.05 mm to about 1.0 mm, more preferably about 0.2 mm to about 0.5 mm.

The length of the engaging portion (hook) 1011 is not particularly limited. Usually, it is preferably about 0.1 mm to about 2.0 mm, more preferably about 0.3 mm to about 1.0 mm. Within such a range of length, the engagement of the engaging members with the first site 1103 can be ensured and detachment from the first site 1103 can be readily manipulated.

It should be noted that in the present invention the shape, structure, number, layout of arrangement and so forth of the engaging members 1010 and holding member 1020 are not limited to those shown in the drawings.

Figure 10A:
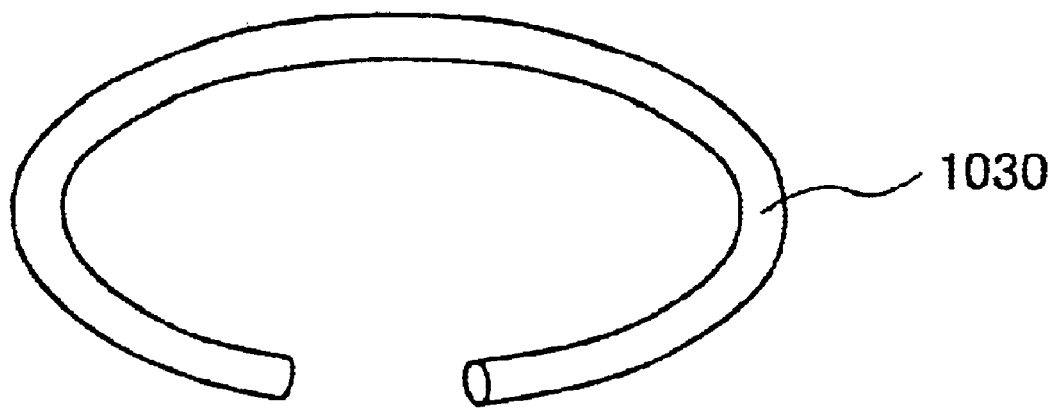
FIG. 10A is a perspective view showing a structure of a fastening member in the blood vessel connecting instrument for use in an end-to-side blood vessel anastomosis method according to the first embodiment of the present invention, illustrating a state of an increased diameter.

A fastening member (fixing instrument) 1030 is wound around the both holding members 1020. The fastening member 1030 is ring-shaped (C-ring) as shown in FIG. 10A and comprises an elastic material. The elastic material includes, for example, metal materials such as stainless steel, titanium or titanium alloys, and superelastic alloys (Ni—Ti based alloys).

Figure 10B:
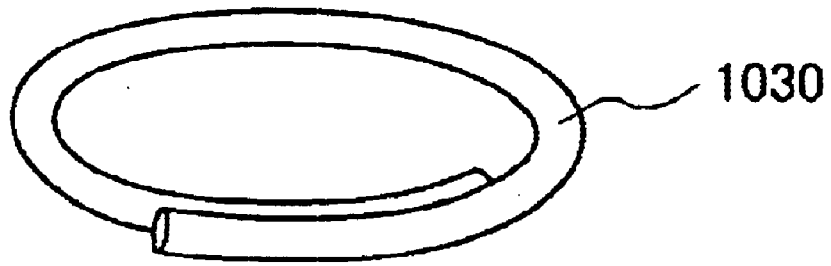
FIG. 10B is a perspective view showing a structure of a fastening member in the blood vessel connecting instrument for use in an end-to-side blood vessel anastomosis method according to the first embodiment of the present invention, illustrating a state of a reduced diameter (in an overlapped state).

The fastening member 1030 in a natural state (in a state where no external force is applied thereto) is constricted to be in a state of a reduced diameter (in a partially overlapped state) as shown in FIG. 10B. Application of a force to the fastening member 1030 as shown in FIG. 10B so as to extend it, it is extended into a state of an increased diameter as shown in FIG. 10A.

Figure 1:
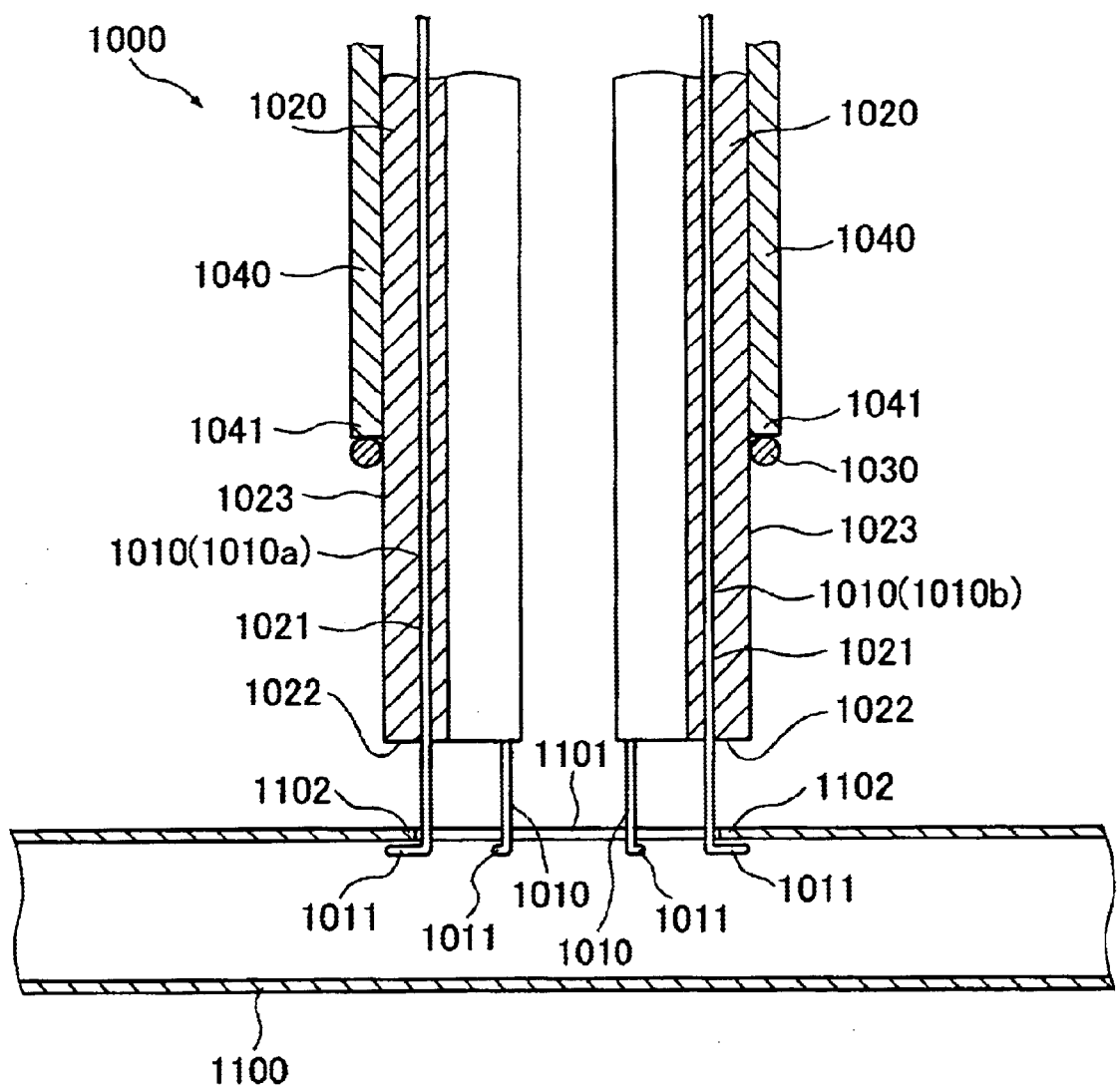
FIGS. 1 to 6 are each a longitudinal cross sectional view showing a blood vessel connecting instrument for use in an end-to-side blood vessel anastomosis method according to a first embodiment of the present invention.

The fastening member 1030 in a state of an increased diameter (the state shown in FIG. 10A) is set around the both holding members 1020 (cf. FIG. 1).

Outside the both holding members 1020, a pressing member 1040 for pressing and moving the fastening member 1030 is arranged as a means for moving the fastening member 1030 to the fixing position of the first blood vessel 1100 and the second blood vessel 1200, i.e., the position where the second site 1300 of the side portion of the first blood vessel and the end portion 1201 of the second blood vessel overlap with each other. Here, the second site of the first blood vessel is at a distance from the peripheral portion 1102 of the opening 1101 greater than the distance of the first site 1103 from the peripheral portion 1102 of the opening 1101.

The pressing member 1040 is arranged so as to be relatively movable in the longitudinal direction with respect to the holding member 1020. On the distal end of the pressing member 1040, a pressing portion 1041 for pressing the fastening member 1030 is formed.

Moving the pressing member 1040 in the direction toward the distal end of the connecting instrument in the state as shown in FIG. 1, for example, to press the fastening member 1030 causes the fastening member 1030 to move in the direction toward the distal end of the connecting instrument, while sliding on the outer peripheries (convex surfaces) 1023 of the both holding members 1020 with maintaining the state of an increased diameter. Therefore, the outer peripheries 1023 of the both holding members 1020 constitute a guide surface (guide portion) for guiding the fastening member 1030 to the fixing position of the first blood vessel 1100 and the second blood vessel 1200.

As shown in FIG. 9, a blood vessel supporting member 1050 supports the second blood vessel 1200 when the first blood vessel 1100 and the second blood vessel 1200 are connected to each other. On this occasion, a ring-shaped receiving member 1060 for receiving fastening force given by the fastening member 1030 is attached to the end portion 1201 of the second blood vessel 1200, so that the second blood 1200 is supported by the receiving member 1060 and the blood vessel supporting member 1050.

The blood vessel supporting member 1050 has a pair of arm portions 1051 whose proximal ends are fixed to each other. The both arm portions 1051 comprise an elastic material, for example, a metal material such as stainless steel or a hard resin. They can become closer to or spaced from each other as a result of elastic deformation.

The distal end portions (bent portions) 1052 of the both arm portions 1051 are respectively bent outwardly and are engaged with the receiving member 1060 so that the dropping off of the receiving member 1060 can be prevented.

The receiving member 1060 may comprise one or more material selected from various metal materials such as stainless steel, titanium or titanium alloys, relatively hard resin materials such as polycarbonate, acrylic resin, polytetrafluoroethylene (Teflon resin), polyethylene, and polypropylene, and ceramic materials such as apatite.

The inner diameter of the receiving member 1060 is preferably substantially identical with the outer diameter of the second blood vessel 1200.

A groove 1061 is formed on the entire outer periphery of the receiving member 1060. The groove 1061 has an arcuately curved concave surface. Provision of the groove 1061 having such a construction can further ensure clipping and fixing the wall of the first blood vessel 1100 and the wall of the second blood vessel 1200 when fastened by means of the fastening member 1030, so that dislocation, breakaway disengagement and so forth of the fastening member 1030 can be prevented.

In particular, since the groove 1061 has an arcuately curved concave surface, the receiving member 1060 can establish an excellent contact with the walls of blood vessels so that blood leakage and so forth can be securely prevented.

Next, the end-to-side blood vessel anastomosis method according to a first embodiment of the present invention will be illustrated using the blood vessel connecting instrument 1000.

[1] A side portion of the first blood vessel (for example, a bypass blood vessel such as a coronary artery) 1100 is partially dissected in the longitudinal direction to form a linear opening 1101.

[2] The blood vessel connecting instrument 1000 is arranged in a state where each engaging member 1010 is projected from the top surface 1022 of the holding member 1020 by a sufficient length. Then, the distal end portion of each engaging member 1010 is inserted in the opening 1101 and the engaging portion 1011 thereof is abutted against the first site (inner side of the blood vessel wall) 1103 in the vicinity of the peripheral portion 1102 of the opening 1101 (cf. FIGS. 1 and 8). On this occasion, each engaging portion 1011 is adjusted so as to have a posture of extending radially outwardly from the center of the opening 1101. Further, by adjusting the distance between the both holding members 1020 the engaging members 1010a and 1010b are arranged respectively so as to be positioned on the both ends of the opening 1101 in the longitudinal direction thereof.

Figure 2:
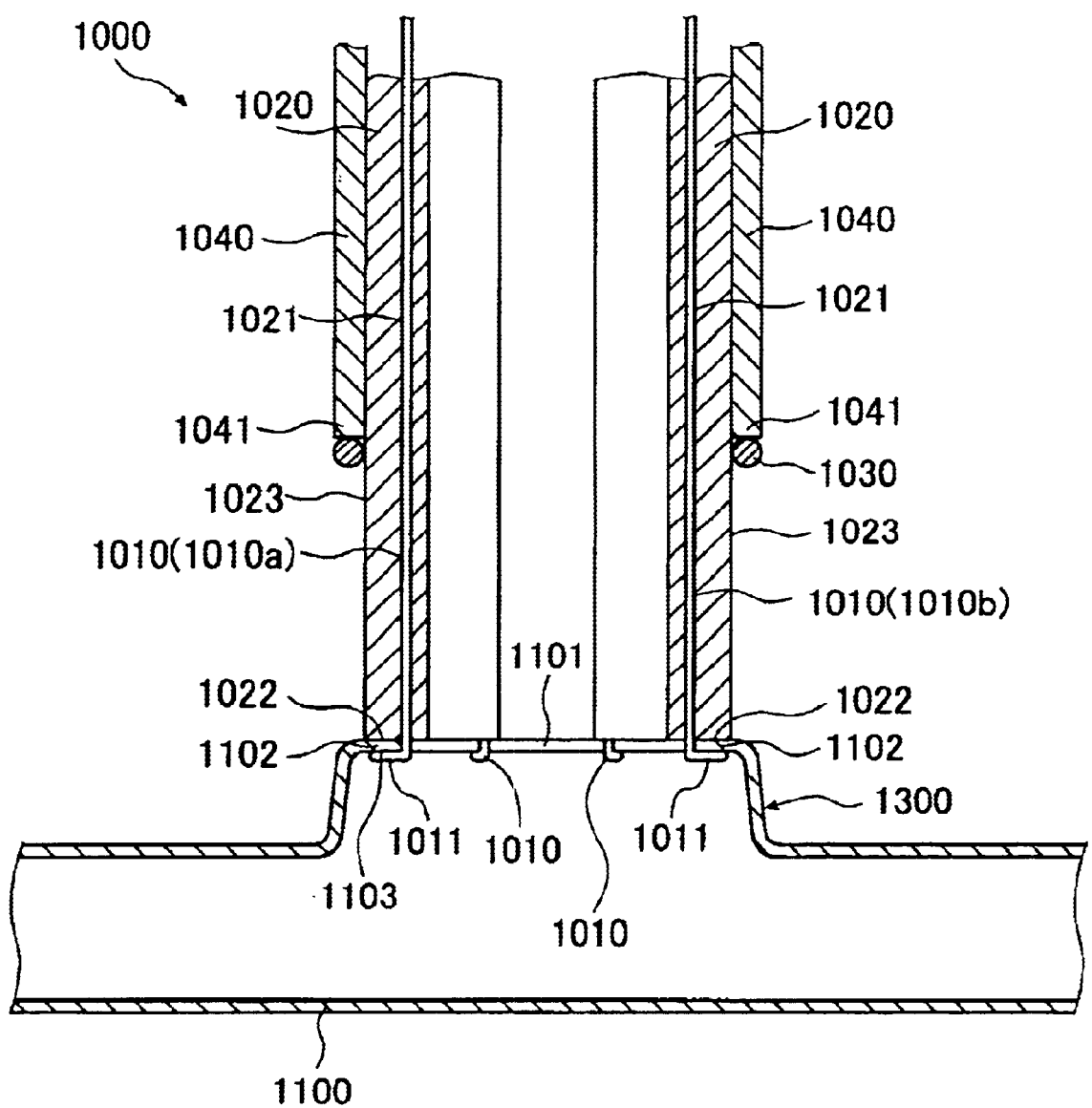

[3] By pulling each engaging member 1010 in the direction toward the proximal end of the connecting instrument or moving the holding members 1020 in the direction toward the distal end of the connecting instrument, the blood vessel connecting instrument 1000 is moved in the direction toward proximal end thereof while clipping the blood vessel wall at the first site 1103 by the engaging portion 1011 and the top surface (clipping portion) 1022 of the holding member 1020 to partially elevate the side portion of the first blood vessel 1100 (cf. FIG. 2). A protruded portion of the first blood vessel 1100 formed by the elevation serves as the fixing position (second position) 1300 for fixing the first blood vessel 1100 and the second blood vessel 1200 to each other.

[4] On the other hand, the second blood vessel (for example, a blood vessel to be bypassed, such as an inner thoracic artery) 1200 is supported by the blood vessel supporting member 1050. This is achieved by the following method.

The both arm portions 1051 of the blood vessel supporting member 1050 are pressed in the directions indicated by the arrows in FIG. 9 to temporarily make them closer to each other so that their distal end portions 1052 can be inserted inside the receiving member 1060 and then the pressing force is released. This generates a force that makes the both arm portions 1051 to be spaced from each other so that the both arm members 1051 can be abutted against the inner surface of the receiving member 1060 and at the same time the distal end portions 1052 can be engaged with the distal end of the receiving member 1060 and be held. In this state, the second blood vessel 1200 is inserted between the both arm portions 1051 and its distal end portion (end portion) 1201 is turned inside out to be reversed it. This is used to cover over the receiving member 1060 (cf. FIG. 9).

Figure 3:
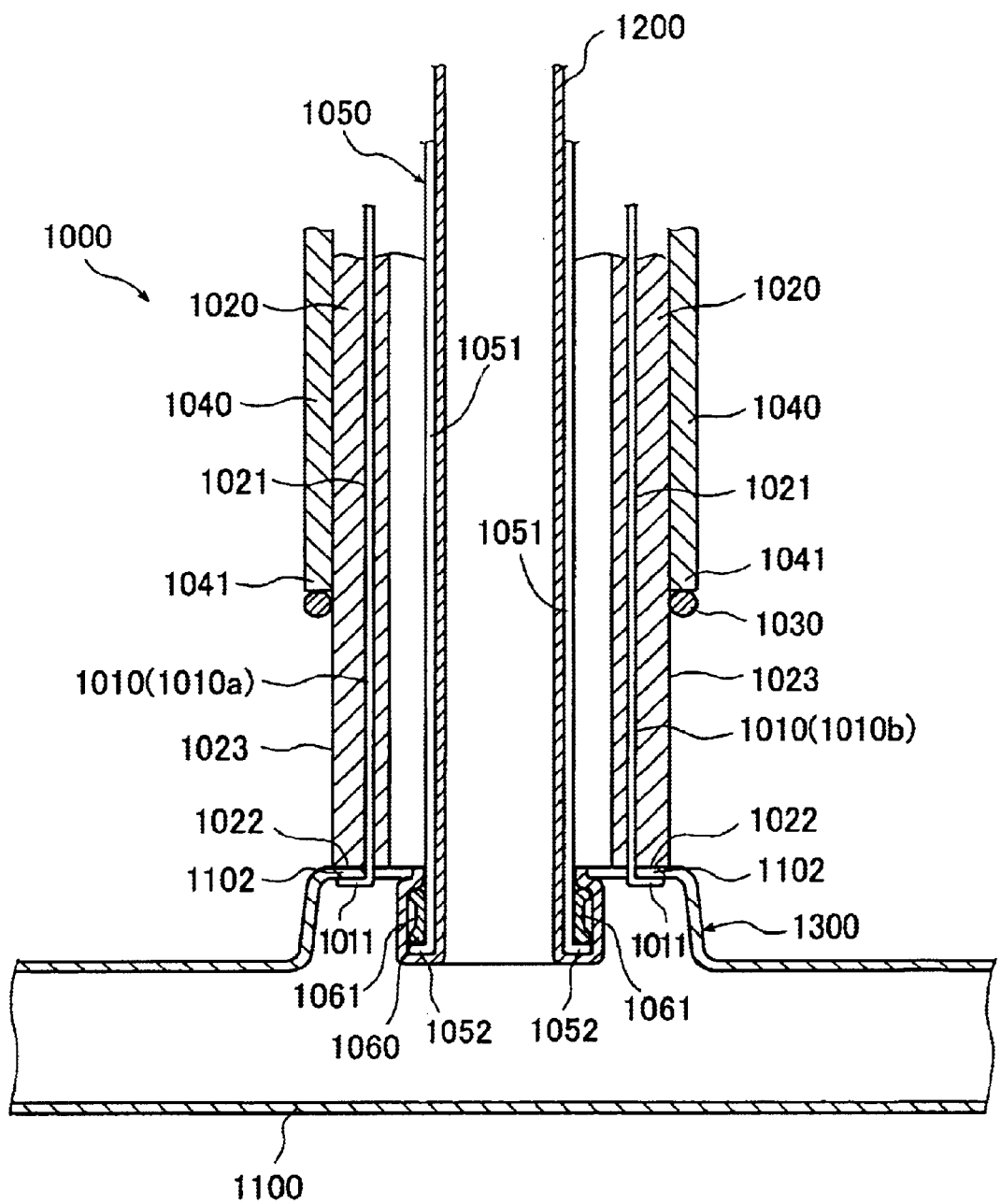
Figure 4:
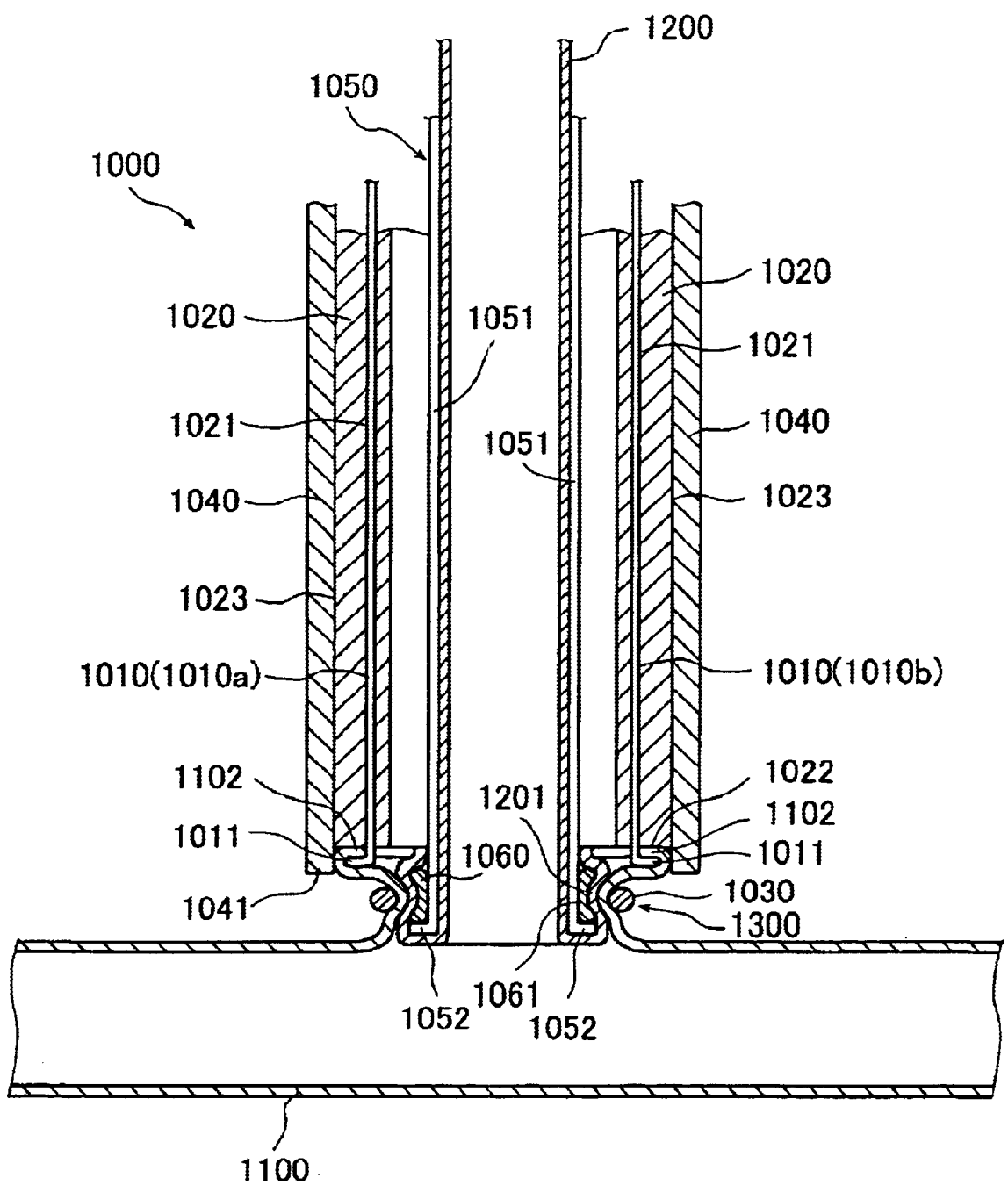
Figure 5:
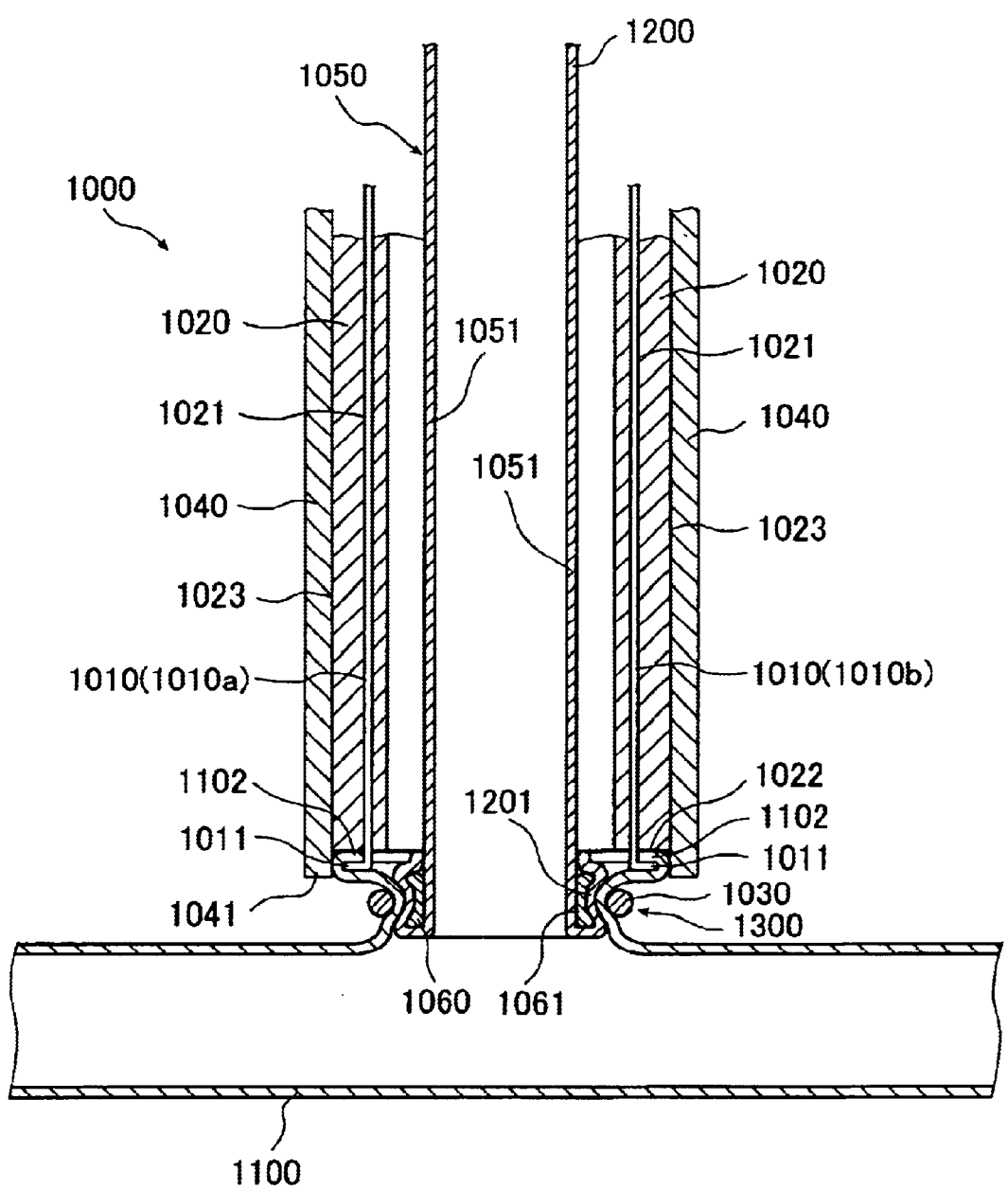

[5] The second blood vessel 1200 supported by the blood vessel supporting member 1050 is inserted between the both holding members 1020 and positioned such that the receiving member 1060 covered with the second blood vessel 1200 is placed at the fixing position, i.e., at the position where it overlaps the second position 1300 of the first blood vessel (cf. FIG. 3).

[6] The pressing member 1040 is moved in the direction toward the distal end portion relative to the holding members 1020 to press the fastening member 1030. As a result of this, the fastening member 1030 moves in the direction toward the distal end, while sliding on the outer peripheries 1023 of the both holding members 1020, with the state of an increased diameter (the state shown in FIG. 10A) maintained. When the fastening member 1030 exceeds the distal ends of the holding members 1020, the reaction force applied by the holding members 1020 disappears. As a result, the fastening member 1030 is constricted to have a reduced diameter due to its own contractile force (elastic force) as shown in FIG. 10B. This causes the overlapping portions of the second blood vessel 1200 and the first blood vessel 1100, i.e., the overlapping portions of the end portion 1201 of the second blood vessel and the second site 1300 of the first blood vessel, to be clipped between the fastening member 1030 and the receiving member 1060 over their entire periphery and fixed therebetween (cf. FIG. 4).

The receiving member 1060 is formed of a groove 1061 so that a firm and secure fixing and connection thereof can be achieved as described above. As a result the dislocation or disengagement between the fastening member 1030 and the receiving member 1060 can be prevented and also excellent fluid seal can be obtained so that there occurs no blood leakage.

The distance between the second site 1300 of the first blood vessel and the peripheral portion 1102 of the opening 1101 is greater than the distance between the peripheral portion 1102 of the opening 1101 and the position where the engaging portion 1011 of each engaging member 1010 is engaged with the inner surface (endoderm) of the first blood vessel 1100, i.e., the first site 1103. This gives rise to the following effects.

That is, the first site 1103 against which the engaging portion 1011 on the inner surface of the first blood vessel 1100 is abutted has the possibility of forming thrombi when it is brought in contact with blood flow due to a wound or the like. However, the first site 1103 is positioned outside the connection site of the blood vessels because the distance of the second site 1300 from the peripheral portion 1102 of the opening 1101 is greater than that of the first site 1103 from the peripheral portion 1102 of the opening 1101 so that it does not contact the blood flow (cf. FIGS. 6 and 8). Therefore, formation of thrombi can be suppressed.

[7] Then, the blood vessel supporting member 1050 is detached (cf. FIG. 5) by the following method. That is, while pressing the both arm portions 1051 in the directions as indicated by the arrows in FIG. 9 so that they can get closer to each other, the distal end portions 1052 of the both arm portions 1051 are withdrawn from inside of the receiving member 1060 and the both arm portions 1051 are pulled in the direction toward proximal end thereof.

Figure 6:
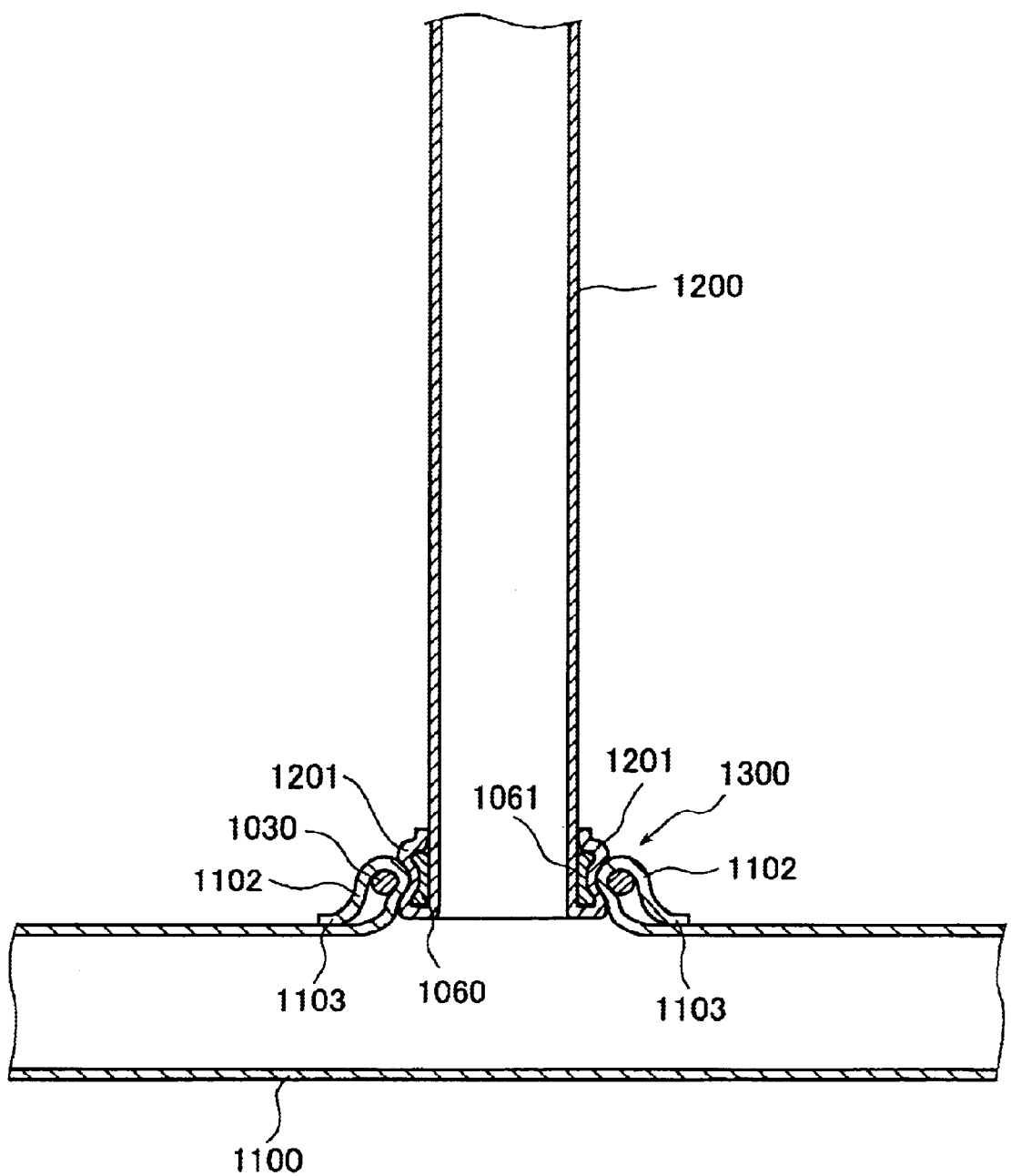

[8] Finally, the blood vessel connecting instrument 1000 is detached and the operation of connection (anastomosis) of the first blood vessel 1100 and the second blood vessel 1200 with each other is completed (cf. FIG. 6).

The operation of detaching the blood vessel connecting instrument 1000 can be performed as follows. First, the both holding members 1020 are moved in the direction toward the proximal end thereof with respect to each engaging member 1010 to release the clipping of the blood vessel wall at the first site 1103 of the first blood vessel 1100. Then, the engaging portion 1011 of each engaging member 1010 is detached from the first site 1103 of the first blood vessel 1100. Thereafter, the blood vessel connecting instrument 1000 is moved in the direction toward the proximal end thereof.

The operation of detaching the engaging portion 1011 from the first site 1103 of the first blood vessel 1100 is performed preferably sequentially for each engaging member 1010. This process can be performed with ease, for example, by rotating the engaging member 1010 so that the engaging portion 1011 can be directed toward the center of the opening 1101.

The first blood vessel 1100 and the second blood vessel 1200 thus anastomosed through the steps as described above are connected to each other firmly and securely and are prevented or suppressed from forming thrombi in the vicinity of the connected portion so that good conditions for patients can be maintained for a long term.

<Second Embodiment>

Figure 11:
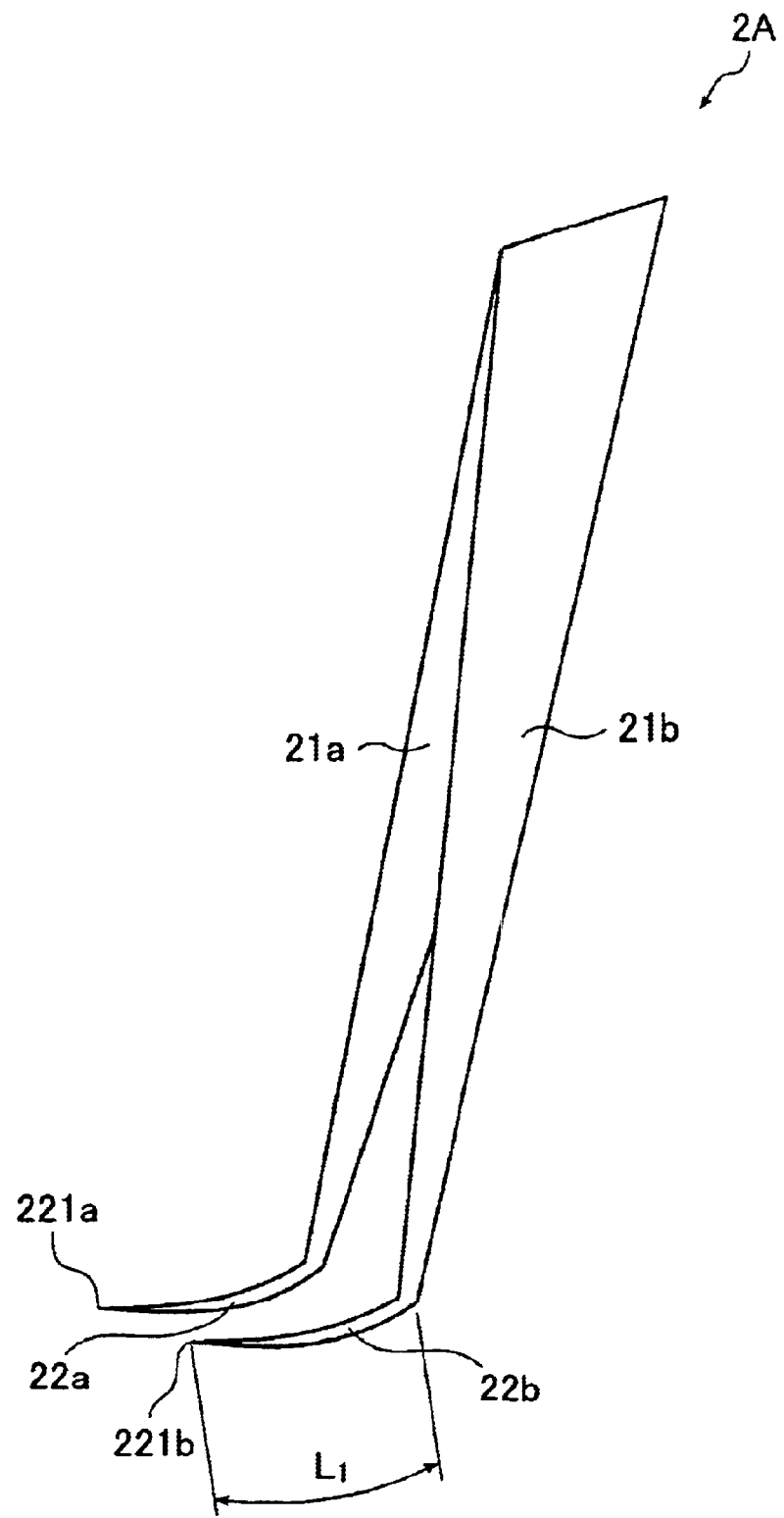
FIG. 11 is a perspective view showing a blood vessel supporting instrument for use in the end-to-side blood vessel anastomosis method according to a second embodiment of the present invention.

FIG. 11 is a perspective view showing a blood vessel supporting instrument for use in the end-to-side blood vessel anastomosis method according to a second embodiment of the present invention. FIGS. 12 to 18 are schematic perspective views, respectively, illustrating in sequence the end-to-side blood vessel anastomosis method using this blood vessel supporting instrument according to a second embodiment of the present invention. In the following explanation, the upper side and lower side in FIG. 1 are referred to as "proximal end" and "distal end", respectively.

First, the blood vessel supporting instrument for use in the end-to-side blood vessel anastomosis method according to a second embodiment of the present invention will be illustrated in detail with reference to FIG. 11.

A blood vessel supporting instrument 2A shown in FIG. 11 comprises a pair of plate-like arm portions 21a and 21b and needle portions 22a and 22b provided on the distal ends (one end portions) of the both arm portions 21a and 21b.

The blood vessel supporting instrument 2A are contemplated to have the both needle portions 22a and 22b pierced (spit) into a blood vessel so as to support a part of the blood vessel to thereby facilitate the dissection and suture of blood vessels.

The arm portions 21a and 21b comprises a metal material such as, stainless steel, aluminum, aluminum alloy, or titanium or titanium alloy and is elastic. The arm portions 21a and 21b are fixed (connected) to each other at proximal end portions (the other end portions) thereof and are capable of pivoting (opening and closing) due to their elastic deformation. The arm portions 21a and 21b are constructed such that in their natural state (the state where no external force is applied thereto) they maintain the state where the both needle portions 22a and 22b are remote from each other (the state where the both arm portions 21a and 21b are open) due to their elasticity.

On the distal end portions (one end portions) of the both arm portions 21a and 21b are provided needle portions 22a and 22b, respectively, so that they are projected therefrom. Preferably, the needle portions 22a and 22b are formed as being projected in the direction at an angle of about 90 to about 150° with respect to the distal end side of the arm portions 21a and 21b, respectively. It is also preferred that the both needle portions 22a and 22b be arranged substantially in parallel to each other.

With the above-mentioned structure, by gripping the arm portions 21a and 21b by the hand or other operation, the both arm portions 21a and 21b get to closer to each other so that the distance between the both needle portions 22a and 22b can be varied (narrowed). This enables one to perform appropriate adjustment of the distance between the both needle portions so that the blood vessels can be supported under optimal conditions depending on the outer diameter of blood vessel, disease of the site to be anastomosed and so forth.

In the present invention, the blood vessel supporting instrument 2A may be the one of which the distance between the both needle portions 22a and 22b is fixed.

The distance between the both needle portions 22a and 22b in their natural state preferably is set smaller than the outer diameter of the blood vessel to be anastomosed.

The transverse cross sectional shape of the needle portions 22a and 22b is preferably of an approximately circular form or approximately ellipsoidal form. In other words, the transverse cross sectional shape of the needle portions 22a and 22b has substantially no corner. This construction prevents occurrence of cuts from the holes formed when they are pierced into the blood vessel so that the wound formed in the blood vessel when it is pierced (spit) can be maintained minimal.

At the terminal ends of the needle portions 22a and 22b, sharp needle points 221a and 221b are formed. The outer diameter of the needle portions 22a and 22b are gradually decreased toward the direction of the needle points 221a and 221b, respectively.

Preferred length of the needle portions 22a and 22b (the length indicated by L1 in FIG. 11) may vary depending on the kind and application of the blood vessel connecting instrument. Usually, the length is preferably 1.5 mm to 40.0 mm and more preferably 2.0 mm to 15.0 mm.

In the construction illustrated in the drawings, the needle portions 22a and 22b as a whole have a curved shape slightly curved with the upper side of FIG. 11 being the inner side of the curve. It is preferred that the entire shape of the needle portions 22a and 22b be of a curved shape close to a straight line or of a straight line shape.

Next, with reference to FIGS. 12 to 18, the end-to-side blood vessel anastomosis method according to the second embodiment of the present invention in which the side portion of a first blood vessel (for example, a coronary artery) 10 and the end portion of a second blood vessel 20 (for example, inner thoracic artery) are anastomosed each other with a ring-shaped fixing instrument 70, by using the blood vessel supporting instrument 2A shown in FIG. 11 will be illustrated in sequence.

Figure 12:
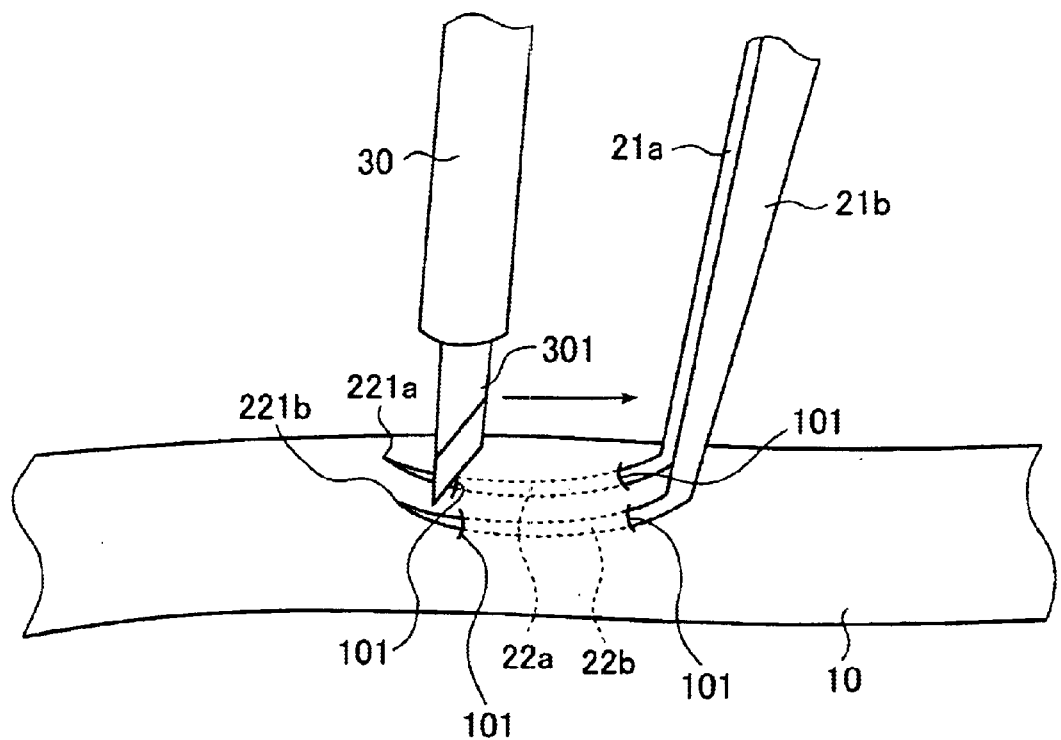
FIGS. 12 to 18 are schematic perspective views, respectively, illustrating in sequence the end-to-side blood vessel anastomosis method according to the second embodiment of the present invention.

[1] As shown in FIG. 12, the needle portions 22a and 22b are pierced into a side portion of the first blood vessel 10 in the state where the both needle portions 22a and 22b of the blood vessel supporting instrument 2A are close to each other. In the case of the blood vessel supporting instrument 2A shown in FIG. 11, the operation of rendering the both needle portions 22a and 22b closer to each other can be performed by gripping the arm portions 21a and 21b of the blood vessel supporting instrument 2A by the hand.

On this occasion, preferably, the needle portions 22a and 22b in the state where the piercing is completed are substantially parallel to the longitudinal direction of the first blood vessel 10. The needle portions 22a and 22b are pierced into the first blood vessel 10 such that the needle points 221a and 221b of the needle portions 22a and 22b, respectively, once pass through the inside of the first blood vessel 10 and then are exposed again outside the blood vessel 10. That is, the first blood vessel 10 is formed of 4 holes 101 in total and the needle portions 22a and 22b are inserted through the holes 101. As a result of this, the first blood vessel 10 is in the state where it is supported (held) at sites (first sites) around the four holes 101.

Figure 13:
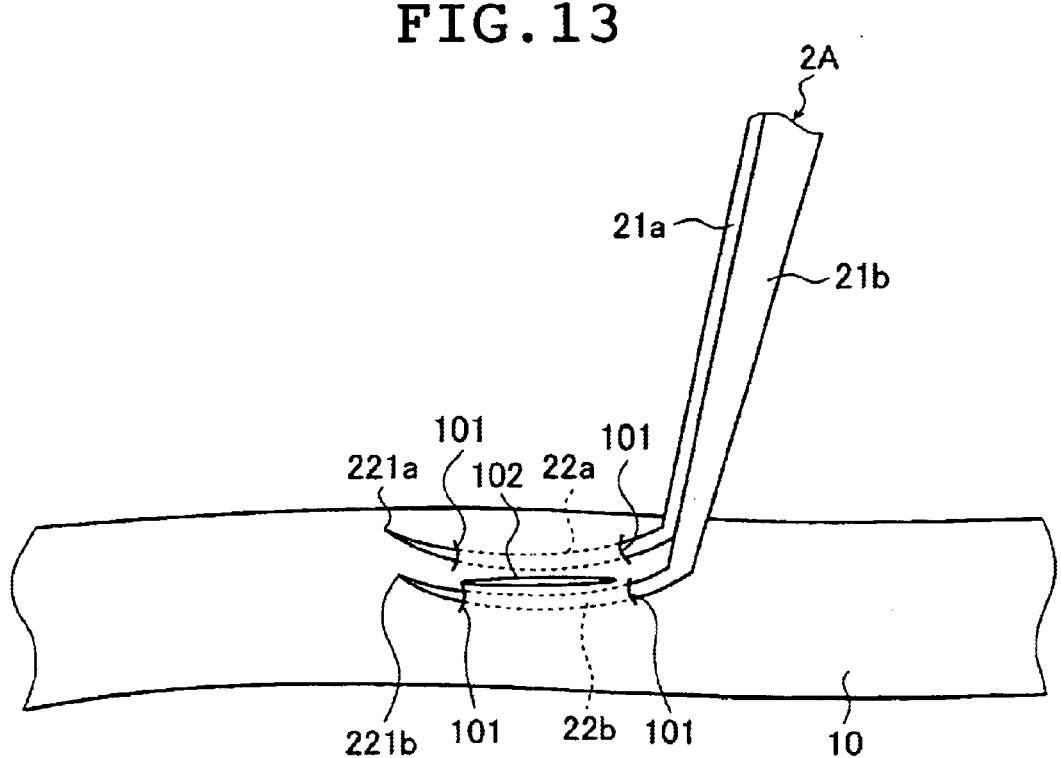

[2] Next, the first blood vessel 10 is partially dissected by a knife 30 to form a linear opening 102 extending in the longitudinal direction of the first blood vessel for communicating with the second blood vessel 20 (FIG. 13). On this occasion, it is preferred that the part of the first blood vessel 10 positioned between the both needle portions 22a and 22b be dissected substantially parallel to the needle portions 22a and 22b.

According to the first embodiment of the method of the present invention, the first site of the first blood vessel 10 is supported and in a stabilized state so that the operation of such dissection can be readily performed.

The first blood vessel 10 may be dissected under tension (tensile force) by slightly expanding the distance between the both needle portions 22a and 22b from each other. This further facilitates the dissection.

Figure 16:
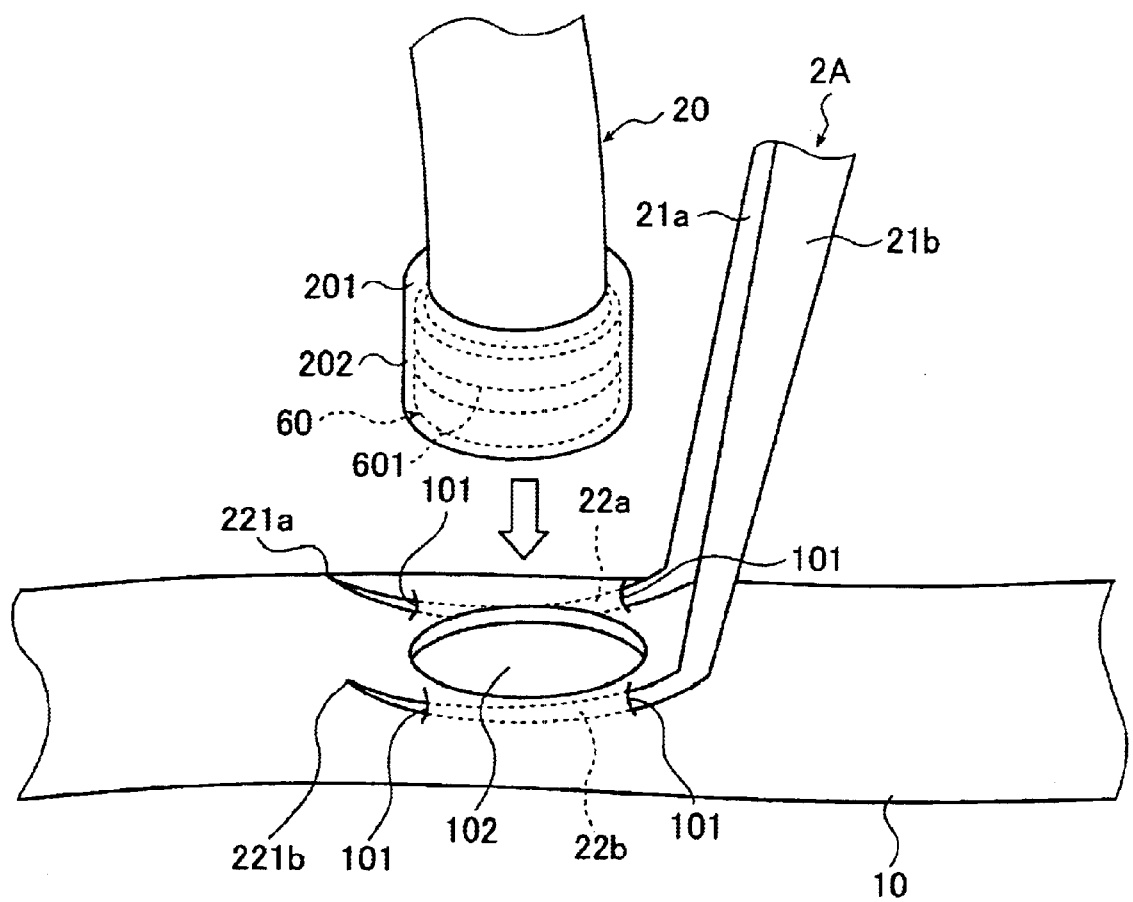

[3] Next, as shown in FIG. 16, the distance between the both needle portions 22a and 22b is increased to broaden (open) the opening 102. With the blood vessel supporting instrument 2A shown in FIG. 1, this operation can be performed by relaxing the closed hand. That is, when releasing the hand that grasps the arm portions 21a and 21b, the distance between the both needle portions 22a and 22b naturally increases due to the elasticity of the arm portions 21a and 21b.

Further, it is possible to relax the grasp of the arm portions 21a and 21b by the hand before the operation of dissection as described in [2] above can be performed so that the opening 102 can be broadened (opened) at the same time with the dissection.

Figure 14:
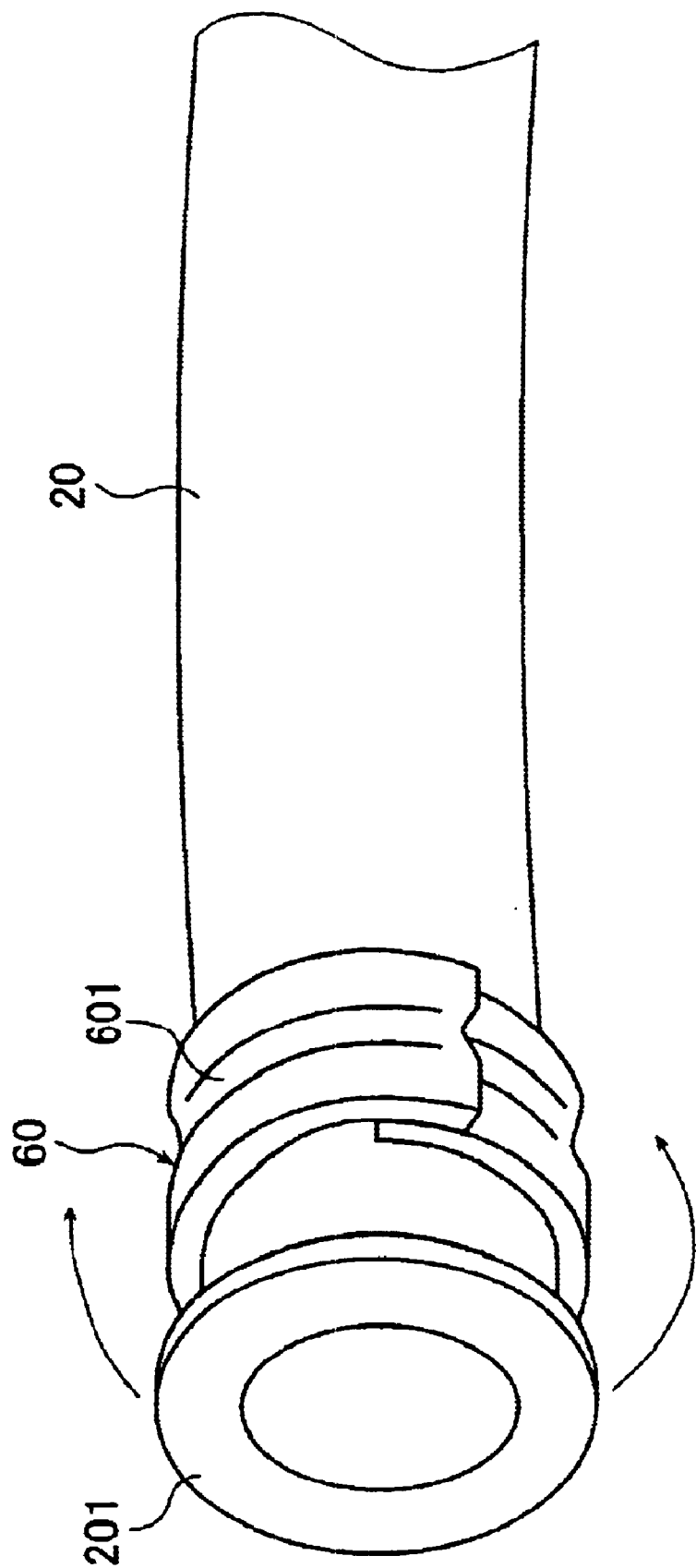

[4] On the other hand, when the opening 102 of the first blood vessel 10 and the distal end portion 202 of the second blood vessel 20 are fixed with a ring-shaped fixing instrument 70, the receiving instrument 60 that receives the fastening force applied by the fixing instrument is attached to the distal end portion 201 of the second blood vessel. First, as shown in FIG. 14, the receiving instrument 60 is inserted into the end portion 201 of the second blood vessel 20. The receiving instrument 60 is tubular or formed by rounding a plate-shaped member. On the outer periphery of the receiving instrument 60, preferably, a groove 601 is formed in the peripheral direction along its entire periphery. This can prevent the dislocation of the fixing instrument 70 described hereinbelow in the axial direction.

Figure 15:
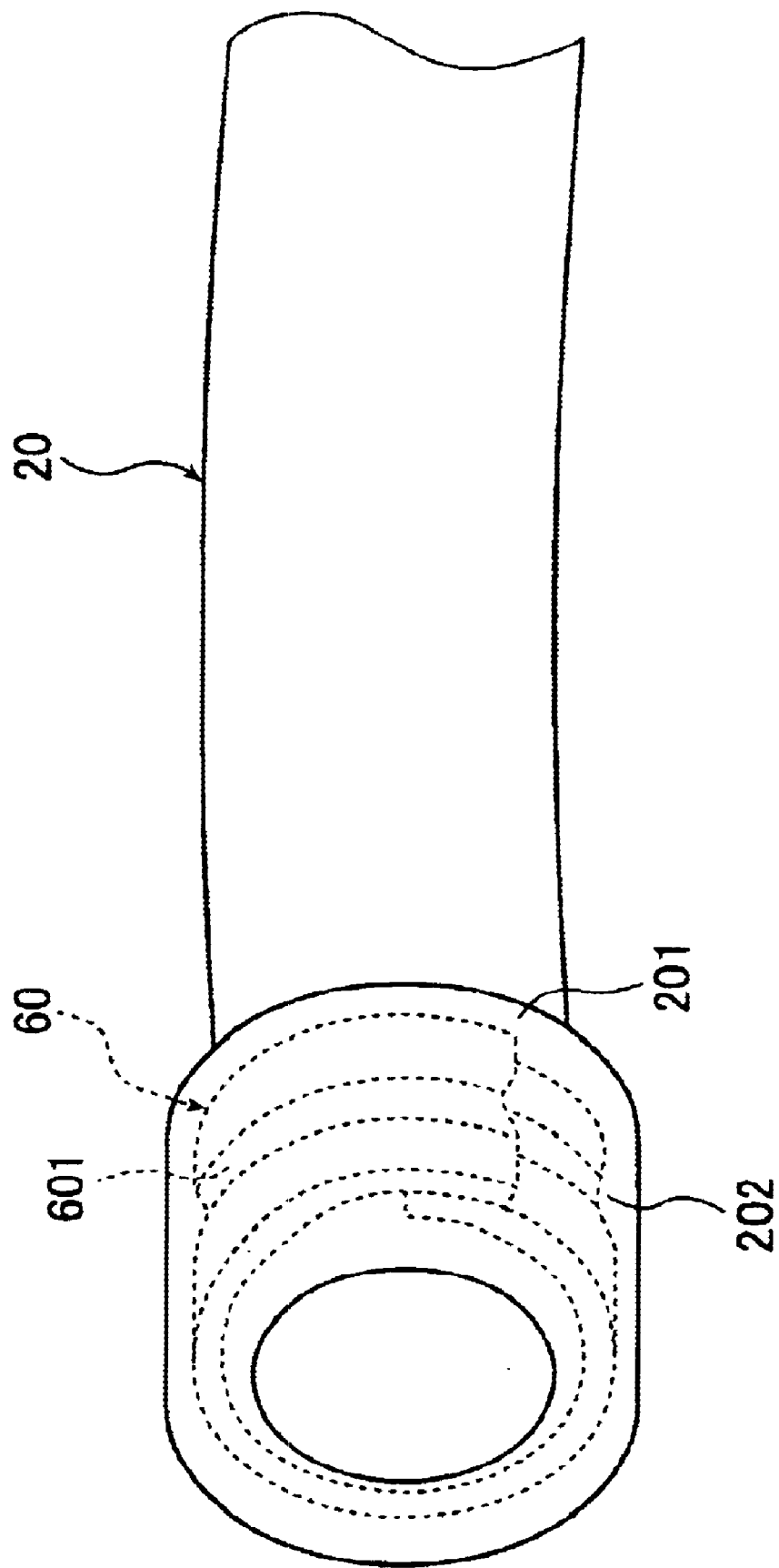

Then, as shown in FIG. 14, the distal end portion 201 of the second blood vessel 20 is folded back toward the receiving instrument 60. As a result, as shown in FIG. 15, the folded portion (end portion) 202 is formed such that the folded portion 202 can envelop (cover) the receiving instrument 60.

As shown in FIG. 16, the folded portion 202 of the second blood vessel 20 is inserted into the opening 102. On this occasion, as described above, the distance of the both needle portions 22a and 22b is increased to broaden the opening 102 so that the operation of insertion can be readily and quickly performed.

Figure 17:
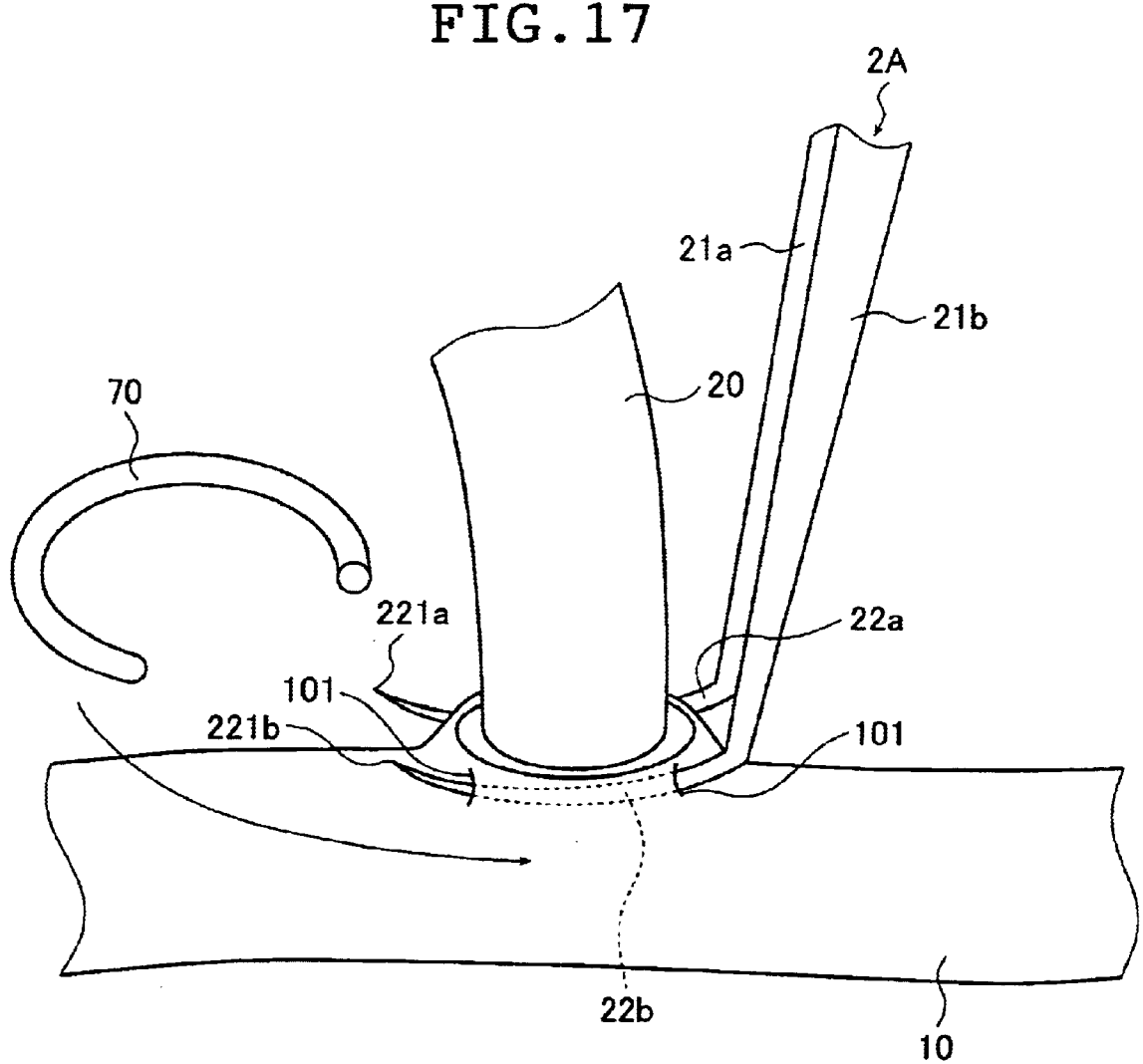
Figure 18:
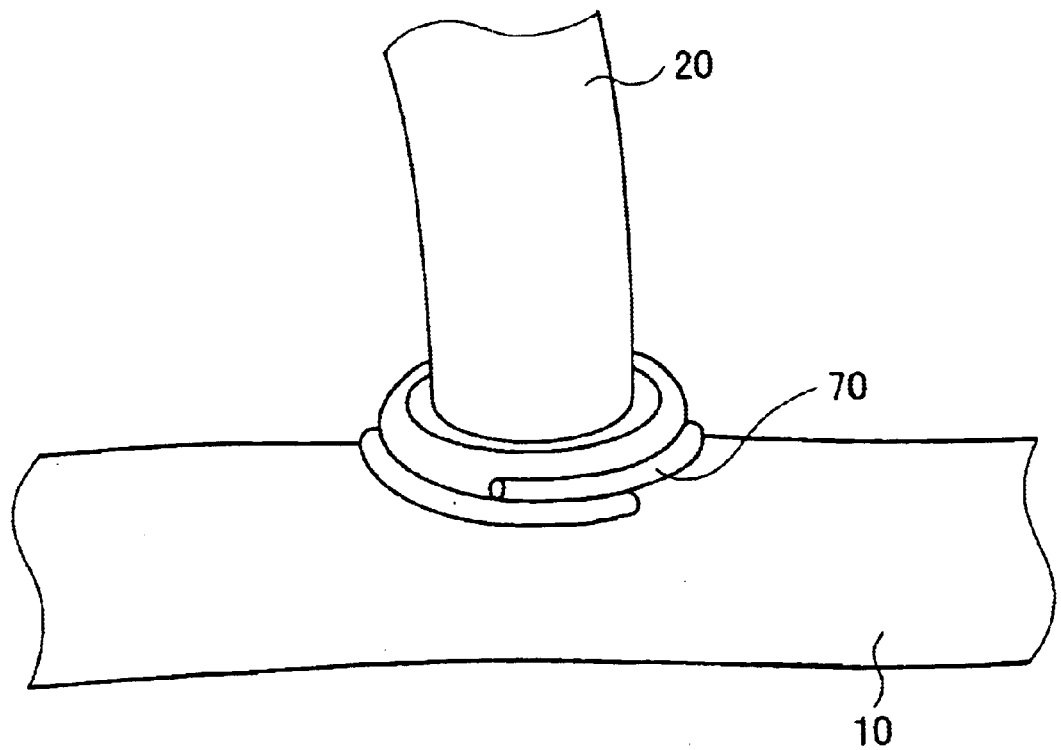

Further, as shown in FIG. 17, the fixing instrument 70 is a member that is a C-shaped as a whole and is circular in transverse cross section. Here, by pulling the arm portions 21a and 21b upward in FIG. 17, a gap for inserting therein the fixing instrument 70 is formed below the needle portions 22a and 22b. The fixing instrument 70 is inserted into the gap. Then, the fixing instrument 70 is caulked (subjected to plastic deformation) so that the diameter thereof can be reduced. As a result, the fixing instrument 70 is deformed into a ring shape, thus completing the anastomosis as shown in FIG. 18.

By pulling the arm portions 21a and 21b upward in FIG. 17, the side portion of the first blood vessel 10 is partially pulled up. As a result, the position at which the first blood vessel is fixed with the fixing instrument (second site) is at a distance from the peripheral portion of the opening 102 greater than the distance of the four holes 101 through which the needle parts 22a and 22b are inserted and sites therearound (first sites) from the peripheral portion of the opening 102. When blood flow contacts the holes 101 through which the needle portions 22a and 22b are pierced, there would be the fear that thrombi could be formed. However, in the present invention, the second site that is fixed by means of the fixing instrument is greater in distance from the opening 102 than the holes 101 and sites therearound (first sites) so that the holes 101 and the sites therearound are positioned outside the blood vessel connection portion. As a result, formation of thrombi can be suppressed.

Note that the transverse cross sectional shape of the fixing instrument 70 is not particularly limited to a circular shape but it may be, for example, a tetragon (rectangle) and so forth.

The outer ring 70, unlike the above-described one, may be ring-shaped in the natural state and expanded into the form of a "C" letter before it can be attached to the first and second blood vessels 10 and 20, respectively, and clip the first blood vessel 10 and the second blood vessel 20 due to its elasticity to connect them.

<Third Embodiment>

Figure 19:
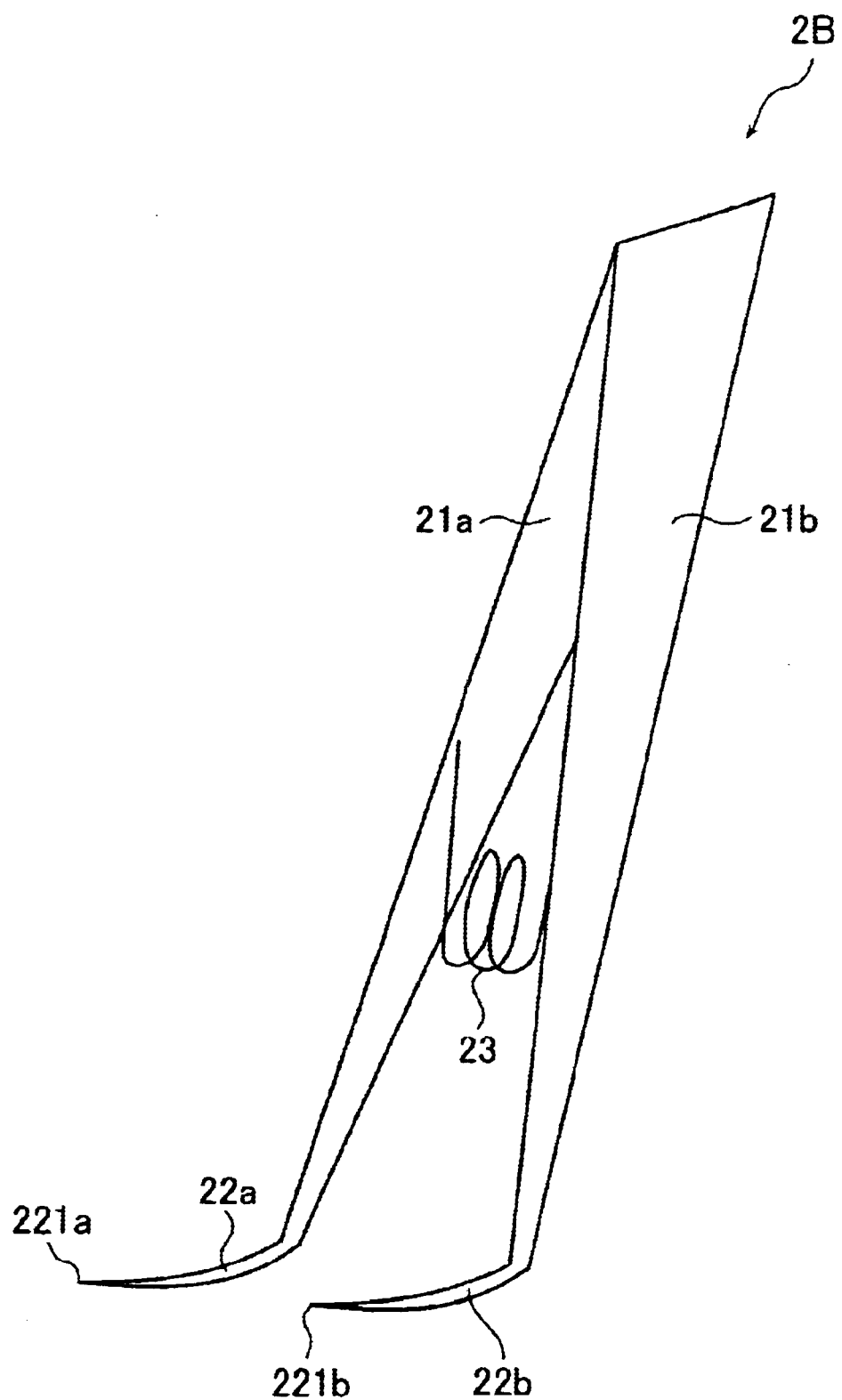
FIG. 19 is a perspective view showing a blood vessel supporting instrument for use in the end-to-side blood vessel anastomosis method according to a third embodiment of the present invention.

FIG. 19 is a perspective view showing a blood vessel supporting instrument for use in the end-to-side blood vessel anastomosis method according to a third embodiment of the present invention. In the following explanation, the upper side and lower side in FIG. 19 are referred to as "proximal end" and "distal end", respectively.

The method of the third embodiment is the same as the method of the previous embodiments except that a blood vessel supporting instrument 2B shown in FIG. 19 is used.

Hereinafter, the method of the third embodiment will be illustrated in detail with reference to FIG. 19. The explanation will be centered on the differences from the methods of the previous embodiments and the explanation on the same or like matter will be omitted.

The blood vessel supporting instrument 2B shown in FIG. 19 is the same as the blood vessel supporting instrument 2A according to the second embodiment above except that an elastic member 23 is arranged between the both arm portions 21a and 21b. In the present embodiment, however, the arm portions 21a and 21b may comprise a material that has substantially no elasticity.

The blood vessel supporting instrument 2B has an elastic member 23 comprising a coil spring arranged to the both arm portions 21a and 21b on the midway in the longitudinal direction thereof. That is, one end of the elastic member 23 is connected to the arm portion 21a and the other end of the elastic member 23 is connected to the arm portion 21b. The both needle portions 22a and 22b are apart from each other in the natural state due to the elasticity of the elastic member 23 and the elasticity of the both arm portions 21a and 21b.

The proximal end portions (other end portions) of the both arm portions 21a and 21b may be fixed to each other in the same manner as the blood vessel supporting instrument 2A described in the second embodiment above. Alternatively, unlike such a construction, it may be connected pivotable by means of a hinge, for example. In that case, the both needle portions 22a and 22b are apart from each other in the natural state due to the elasticity of the elastic member 23 only.

As the elastic member 23, various materials having suitable elasticity, for example, a torsion spring, a leaf spring, rubbery body and so forth may be used.

The use method, operation and effects of the blood vessel supporting instrument 2B are the same as the blood vessel supporting instrument 2A in the second embodiment above.

<Fourth Embodiment>

Figure 20:
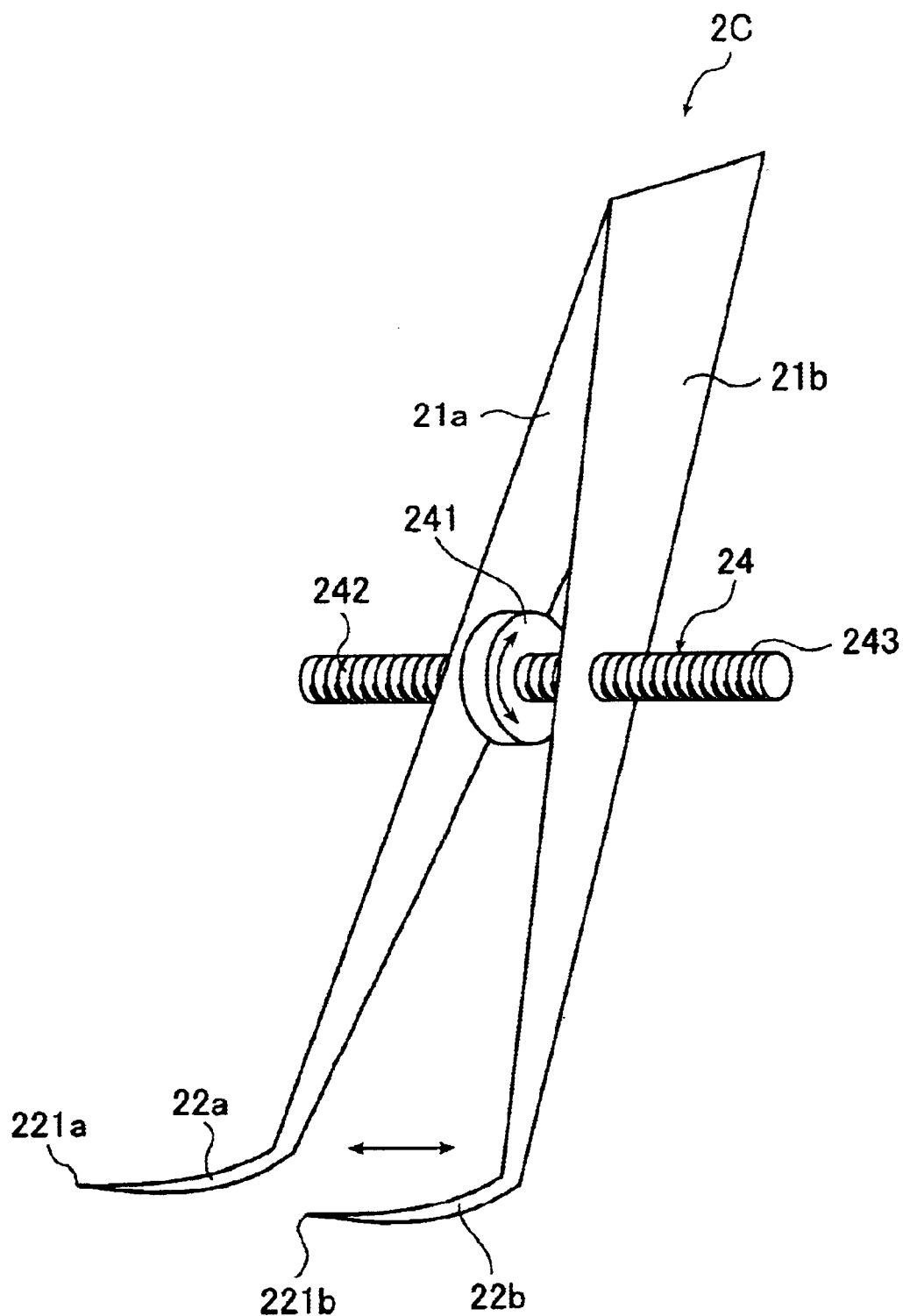
FIG. 20 is a perspective view showing a blood vessel supporting instrument for use in the end-to-side blood vessel anastomosis method according to a fourth embodiment of the present invention.

FIG. 20 is a perspective view showing a blood vessel supporting instrument for use in the end-to-side blood vessel anastomosis method according to a fourth embodiment of the present invention. In the following explanation, the upper side and lower side in FIG. 20 are referred to as "proximal end" and "distal end", respectively.

The method of the fourth embodiment is the same as the method of the second embodiment above except that a blood vessel supporting instrument 2C shown in FIG. 20 is used.

Hereinafter, the method of the fourth embodiment will be illustrated in detail with reference to FIG. 20. The explanation will be centered on the differences from the methods of the previous embodiments and the explanation on the same or like matter will be omitted.

The blood vessel supporting instrument 2C shown in FIG. 20 is the same as the blood vessel supporting instrument 2A according to the second embodiment above except that the distance between the both needle portions 22a and 22b can be adjusted and maintained.

The blood vessel supporting instrument 2C is provided with a turnbuckle 24 arranged at substantially right angles to the both arm portions 21a and 21b on the midway in the longitudinal direction thereof.

On the left-hand side in FIG. 20 of the turnbuckle 24, there is formed a right-hand thread portion 242 in which the right-hand thread is cut. On the right-hand side in FIG. 20 of the turnbuckle 24, there is formed a left-hand thread portion 243 in which the left-hand thread is cut. In the central portion of the turnbuckle 24 in the longitudinal direction, a dial 241 is arranged. The right-hand thread portion 242 of the turnbuckle 24 intermeshes with the arm portion 21a and the left-hand thread portion 243 intermeshes with the arm portion 21b.

The proximal end portions (other end portions) of the both arm portions 21a and 21b may be fixed to each other in the same manner as the blood vessel supporting instrument 2A described in the second embodiment above. Alternatively, unlike such a construction, it may be connected pivotable by means of a hinge, for example. In that case, the both needle portions 22a and 22b are apart from each other in the natural state due to the elasticity of the elastic member 23 only.

With the construction, the distance between the both needle portions 22a and 22b can be freely adjusted by handling the dial 241 to turn the turnbuckle 24. The distance between the both needle portions 22a and 22b can be maintained in a desired state set by the adjustment.

This enables one to freely expand the opening 102 of the first blood vessel 10 to a desired size sufficient for the folded portion 202 of the second blood vessel 20 to be inserted into the opening 102 and for the opening 102 of the first blood vessel 10 to be fixed by means of a fixing instrument 70 when performing the operation of [3] in the method according to the second embodiment above (cf. FIG. 16). In addition, this state can be maintained. As a result, anastomosis of blood vessels can be performed quickly and with ease.

Rotating operation of the dial 241 can adjust the distance between the both needle portions 22a and 22b and hence the micro adjustment of the distance between the needle portions 22a and 22b is easy and a desired distance therebetween can be obtained with ease.

The use method, operation and effects of the blood vessel supporting instrument 2C are the same as the blood vessel supporting instrument 2A in the second embodiment above except the points described above.

<Fifth Embodiment>

Figure 21:
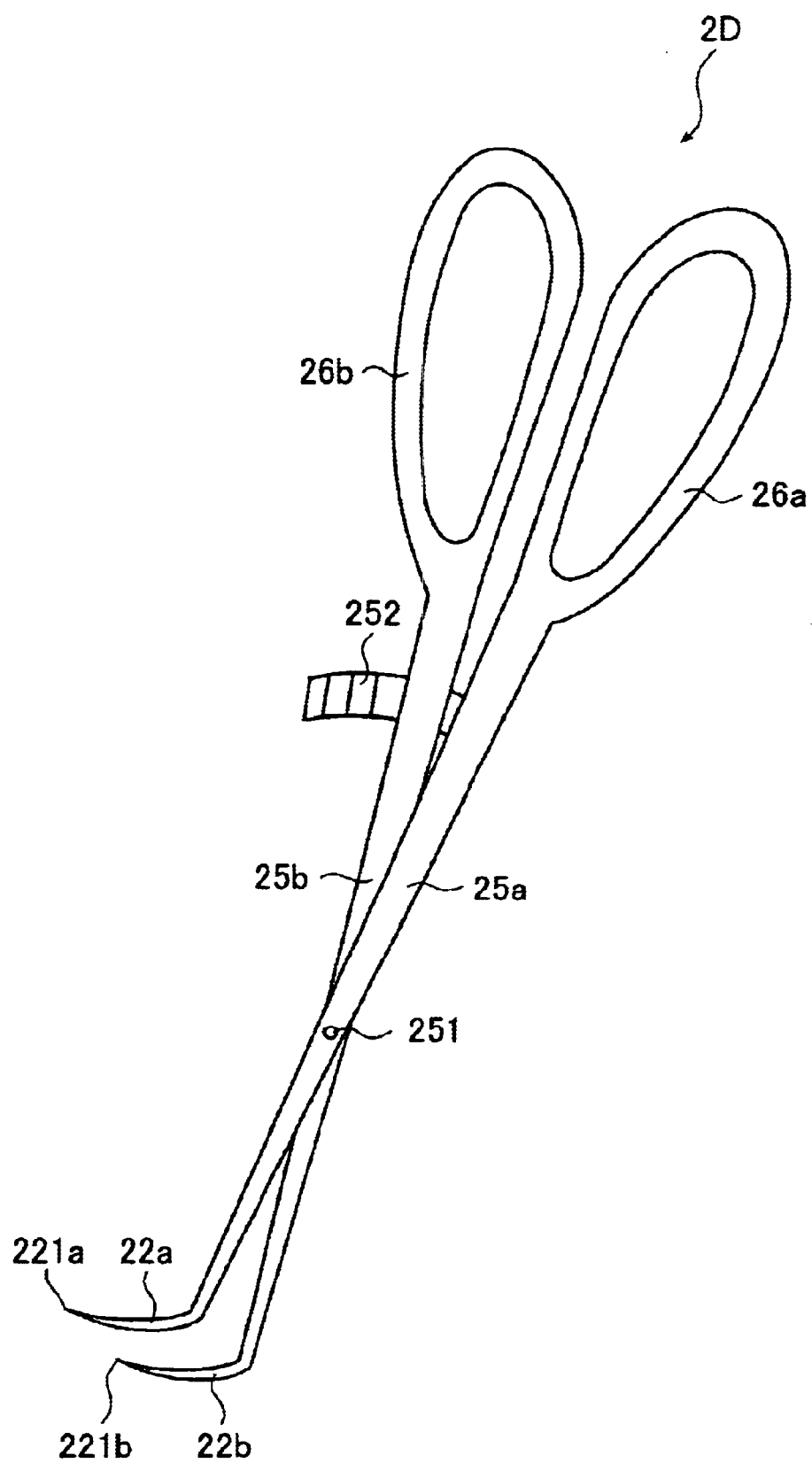
FIG. 21 is a perspective view showing a blood vessel supporting instrument for use in the end-to-side blood vessel anastomosis method according to a fifth embodiment of the present invention.

FIG. 21 is a perspective view showing a blood vessel supporting instrument for use in the end-to-side blood vessel anastomosis method according to a fifth embodiment of the present invention. In the following explanation, the upper side and lower side in FIG. 21 are referred to as "proximal end" and "distal end", respectively.

The method of the fifth embodiment is the same as the method of the second embodiment above except that a blood vessel supporting instrument 2D shown in FIG. 21 is used.

Hereinafter, the method of the fifth embodiment will be illustrated in detail with reference to FIG. 21. The explanation will be centered on the differences from the methods of the second embodiment above and the explanation on the same or like matter will be omitted.

The blood vessel supporting instrument 2D shown in FIG. 21 comprises a pair of arm portions 25a and 25b, needle portions 22a and 22b attached to the distal end portions (one end portions) of the both arm portions 25a and 25b, respectively, and finger insertion portions 26a and 26b attached to the proximal end portions (the other end portions) of the both arm portions 25a and 25b, respectively.

The both arm portions 25a and 25b are connected to each other, for example, through a pin 251 in a crossed state on the midway in the longitudinal direction thereof so that they are pivotal. With this construction, opening or closing the proximal end portions (the other end portions) of the both arm portions 25a and 25b results in opening or closing the distal end portions (one end portions) of the both arm portions 25a and 25b accordingly.

The shape of the needle portions 22a and 22b attached to the distal end portions (one end portions) of the both arm portions 25a and 25b are the same as that of the blood vessel supporting instrument used in the method of the second embodiment above.

The finger insertion portions 26a and 26b attached to the proximal end portions (the other end portions) of the both arm portions 25a and 25b are ring-shaped. The blood vessel supporting instrument 2D is handled in the same manner as scissors by inserting fingers inside the finger insertion portions 26a and 26b, respectively, so as to broaden or narrow the distance between the finger insertion portions 26a and 26b. This enables one to perform the operation of adjustment of the distance between the needle portions 22a and 22b.

A rack 252 is provided on the side of the proximal end of the arm portion 25a and a protrusion or convex portion (not shown) that can contact the rack 252 is arranged on the side of the proximal end of the arm portion 25b. The rack 252 as a whole is of an arcuate shape centered on the connection portion (pin 251) of the both arm portions 25a and 25b and is projected in the direction toward the other arm portion 25b. On the side of the rack 252 that contacts the above-mentioned protrusion, small protrusions and depressions are repeatedly formed in the longitudinal direction thereof. The protrusions are pressed onto the rack 252 due to the elasticity of the both arm portions 25a and 25b.

With such a construction, the state of opening or closing of the arm portions 25a and 25b can be fixed at a desired angle by a force of the protrusions engaging with the protrusions and depressions of the rack 252. As a result, the distance between the both needle portions 22a and 22b adjusted by operating the finger insertion portions 26a and 26b, respectively, can be maintained as it is.

Here, the operation of opening or closing the arm portions 25a and 25b is performed by addition of an operating force identical with or greater than the force for engaging the protrusions and depressions of the rack 252 with the protrusions. Alternatively, operation of the both finger insertion portions 26a and 26b such that they are distorted in the direction in which the protrusion departs from the rack 252 results in an easy release of the engagement of the protrusion with the rack 252. As a result, the arm portions 25a and 25b can be opened or closed without any resistance.

As explained above, the blood vessel supporting instrument 2D can adjust the distance between the both needle portions 22a and 22b and maintain it as it is. This enables one to freely expand the opening 102 of the first blood vessel 10 to a desired size sufficient for the folded portion 202 of the second blood vessel 20 to be inserted into the opening 102 and for the opening 102 of the first blood vessel 10 to be fixed by means of the fixing instrument 70 in the same manner as in the case of the blood vessel supporting instrument 2C in the fourth embodiment above when performing the operation described in [3] in the method of the second embodiment above (cf. FIG. 16). In addition, this state can be maintained. As a result, anastomosis of blood vessels can be performed quickly and with ease. This enables one to perform anastomosis of blood vessels quickly and with ease.

Further, since the blood vessel supporting instrument 2D can be operated by inserting fingers in the finger insertion portions 26a and 26b, respectively so that it can be handled like scissors, the adjustment of the distance between the both needle portions 22a and 22b can be performed with ease and quickly.

The use method, operation and effects of the blood vessel supporting instrument 2D are the same as the blood vessel supporting instrument 2A in the second embodiment above except the points described above.

<Sixth Embodiment>

Figure 22:
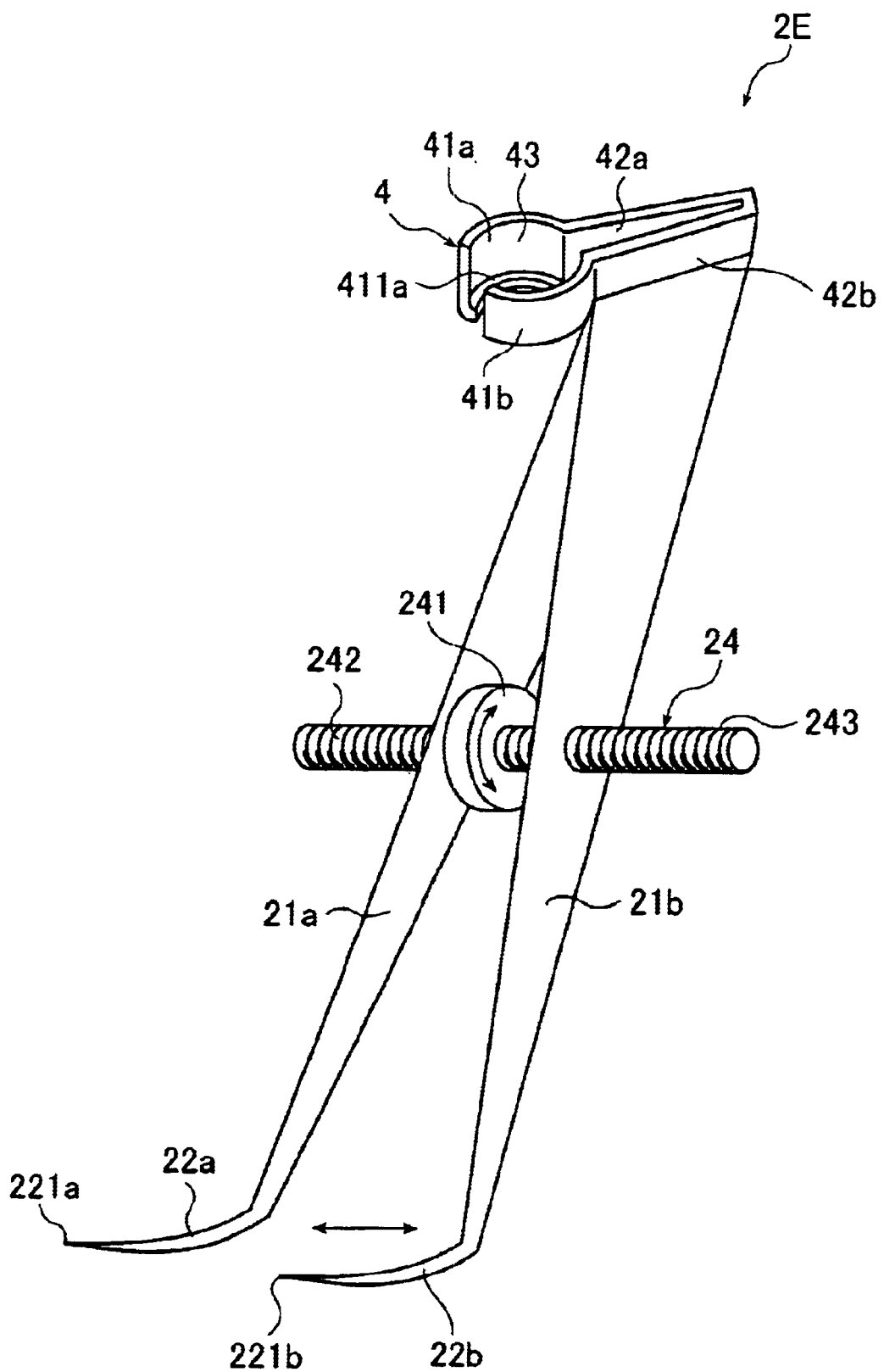
FIG. 22 is a perspective view showing a blood vessel supporting instrument for use in the end-to-side blood vessel anastomosis method according to a sixth embodiment of the present invention.
Figure 23:
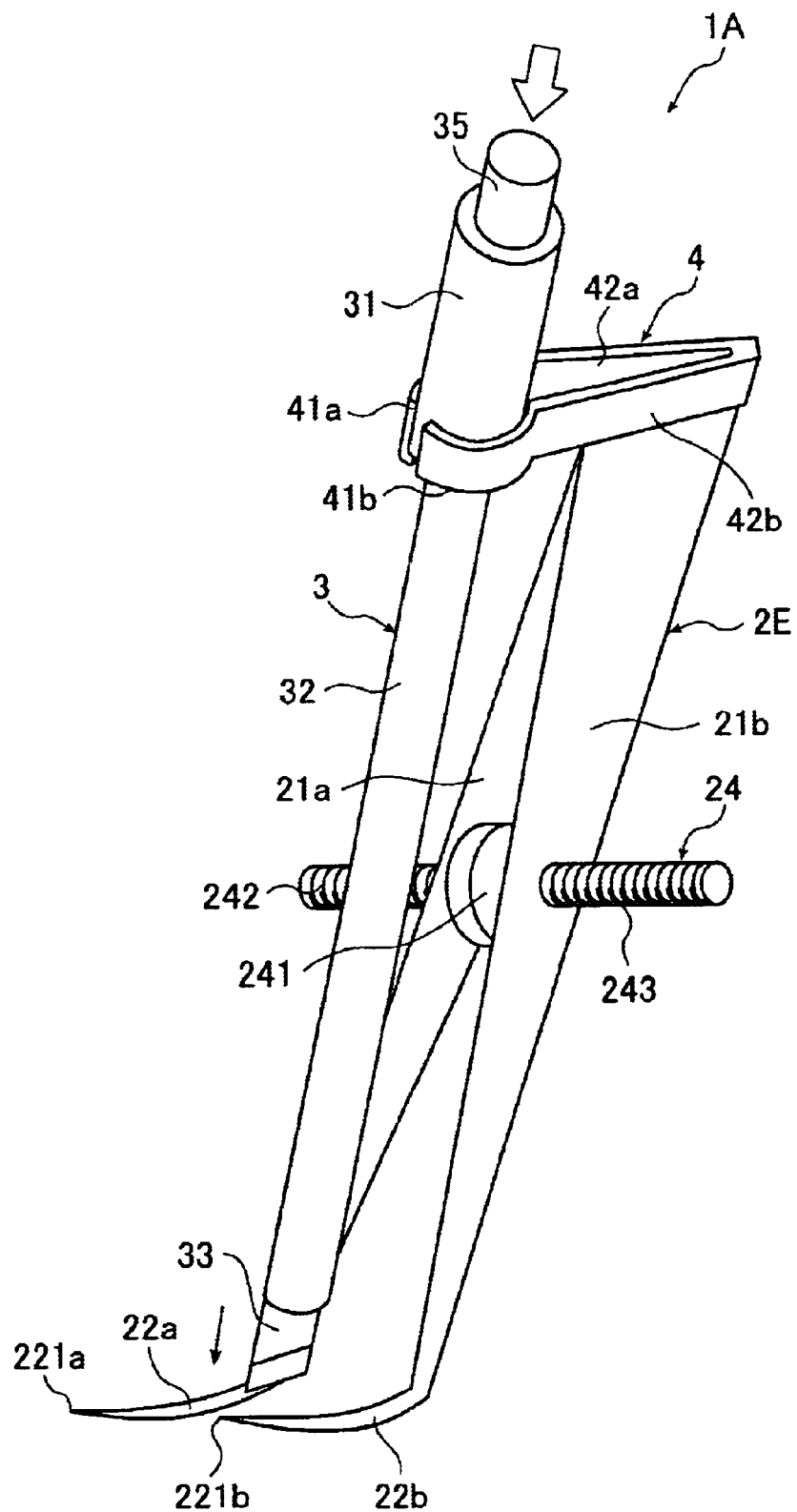
FIG. 23 is a perspective view showing a surgical instrument 1A comprising the blood vessel supporting instrument shown in FIG. 22 and a dissection instrument 3.
Figure 24:
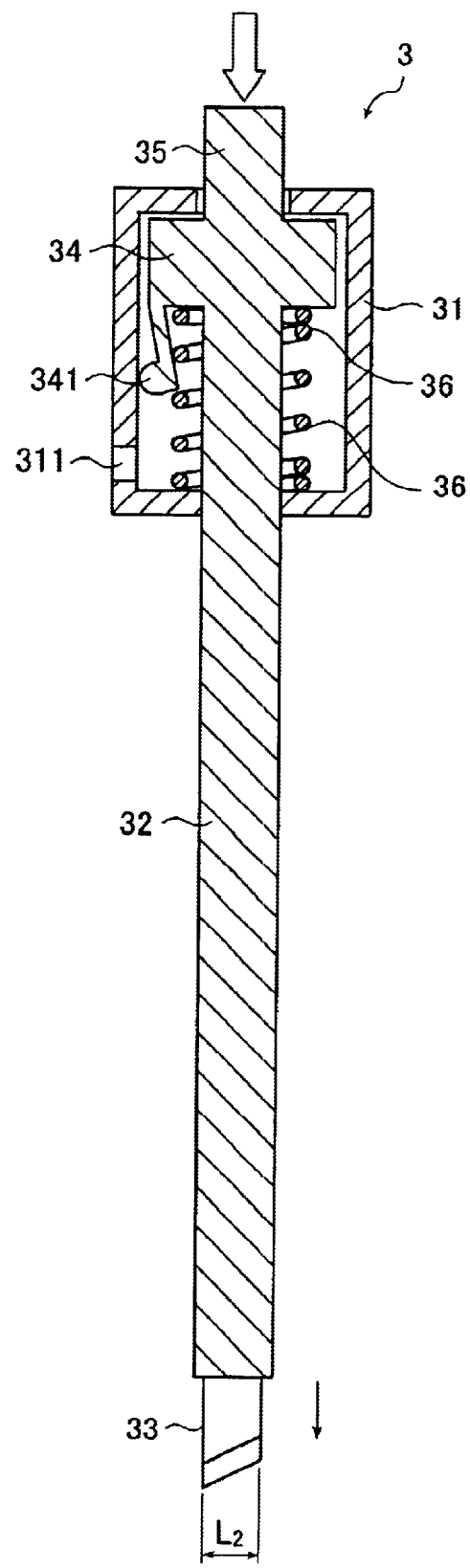
FIG. 24 is a vertical sectional view showing the dissecting instrument shown in FIG. 23.

FIG. 22 is a perspective view showing a blood vessel supporting instrument for use in the end-to-side blood vessel anastomosis method according to a sixth embodiment of the present invention. FIG. 23 is a perspective view showing a surgical instrument 1A comprising a blood vessel supporting instrument 2E shown in FIG. 22 and a dissecting instrument 3. FIG. 24 is a vertical cross sectional view showing the dissecting instrument 3 shown in FIG. 23. In the following explanation, the upper side and lower side in FIGS. 22 to 24 are referred to as "proximal end" and "distal end", respectively. The direction toward the terminal ends of the needle portions 22a and 22b is referred to as "front" and the direction toward the roots of the needle portions 22a and 22b is referred to as "rear".

The method of the sixth embodiment is the same as the method of the second embodiment above except that a surgical instrument comprising a blood vessel supporting instrument and a dissecting instrument is used instead of the blood vessel supporting instrument.

Hereinafter, the method of the sixth embodiment will be illustrated in detail with reference to FIGS. 22 to 24. The explanation will be centered on the differences from the method of the second embodiment and the explanation on the same or like matter will be omitted.

The blood vessel supporting instrument 2E shown in FIG. 22 is the same as the blood vessel supporting instrument 2C according to the fourth embodiment above except that it has a dissecting instrument attaching portion capable of attaching a dissecting instrument that dissects the first blood vessel 10.

As shown in FIG. 22, the blood vessel supporting instrument 2E is provided with a dissecting instrument attaching portion 4 capable of attaching a dissecting instrument 3 at proximal end portions of the arm portions 21a and 21b. The dissecting instrument attaching portion 4 will be illustrated hereinbelow.

The dissecting instrument 3 comprises a knife having a cutter blade 33 as shown in FIGS. 23 and 24. It has a circular cylinder 31, a piston 34 slidably arranged in the cylinder 31, a rod 32 projecting from the distal end of the cylinder 31, a cutter blade (distal end portion) 33 arranged at the distal end portion of the rod 32, and an operation button (operating portion) 35 projecting from the proximal end of the cylinder 31.

In the cylinder 31, a coil spring 36 is arranged. The coil spring 36 urges the piston 34 against the cylinder 31 toward the proximal end thereof. The rod 32 is inserted through the cavity defined by the coil spring 36. Because of the urging force of the coil spring 36, the piston 34 can be positioned in a state where it is abutted at its proximal end surface against the inner wall of the cylinder 31 on the side of the proximal end thereof (the state shown in FIG. 24). The state where the piston 34 is in this position is referred to as "standard state".

The rod 32 and the operation button 35 are each fixed to the piston 34 and arranged coaxially with the piston 34. That is, the rod 32, the piston 34 and the operation button 35 as an integral body can be moved along the cylinder 31 in the axial direction thereof.

As a result, pushing the operation button 35 in the direction toward the distal end (in the downward direction in FIG. 24) can move the piston 34 and the rod 32 toward the distal end of the cylinder 31. The state where the piston 34 is in a position moved toward the distal end is hereinafter referred to as "dislocated state".

An engaging piece 341 is formed as a protrusion from the distal end portion of the piston 34. It projects toward the distal end and an engaging portion constituted by a hole 311 in which the engaging piece 341 can be engaged is provided in the side wall of the distal end portion of the cylinder 31.

The dissecting instrument 3 does not have to be provided with an engagement mechanism constituted by the engaging piece 341 and the hole 311.

Because the piston 34 is capable of dislocation to the standard state and to the dislocated state, the cutter blade 33 of the dissecting instrument 3 can be dislocated to a first position corresponding to the standard state above and to a second position corresponding to the dislocated state. The urging force of the coil spring 36 urges the cutter blade 33 in the direction from the second position toward the first position.

The dissecting instrument attaching portion 4 comprises a pair of holding portions 41a and 41b that hold the distal end of the cylinder 31 of the dissecting instrument 3 on both sides thereof, and supporting portions 42a and 42b supporting the both holding portions 41a and 41b, respectively.

The holding portions 41a and 41b are arranged at the front ends of the supporting portions 42a and 42b, respectively. The holding portions 41a and 41b are each curved and arranged such that the inside portions of the curves oppose to each other. This forms a gap 43 having a form corresponding to the cylinder 31 between the both holding portions 41a and 41b.

The supporting portions 42a and 42b have elasticity and rear ends thereof are fixed to each other. Because of the elasticity of the supporting portions 42a and 42b, the distance between the both holding portions 41a and 41b in the natural state is decreased, i.e., they are in a state of getting closer to each other.

When the distal end side of the cylinder 31 of the dissecting instrument 3 is inserted between the holding portions 41a and 41b, the gap 43 is broadened so that the supporting portions 42a and 42b undergo elastic deformation. As a result, the holding portions 41a and 41b hold (clip) the distal end side of the cylinder 31 due to the elastic force of the supporting portions 42a and 42b, respectively.

Flanges 411a and 411b that project inwardly are formed at the distal end portions of the holding portions 41a and 41b, respectively. By abutting the distal end of the cylinder 31 against the proximal end surface of the flanges 411a and 411b, the dissecting instrument 3 can be attached to the blood vessel supporting instrument 2E by being positioned in upward and downward directions in FIG. 22.

This kind of dissecting instrument 3 can be attached to the dissecting instrument attaching portion 4 of the blood vessel supporting instrument 2E preferably in a detachable manner. The blood supporting instrument 2E and the dissecting instrument 3 together constitute the surgical instrument 1A of the present invention.

Here, the construction of the dissecting instrument attaching portion 4 is not limited to the above-described ones and any means may be used to which the dissecting instrument can be attached. For example, those constructions utilizing fitting, screwing, absorption with a magnet or the like method may be used. Also, constructions utilizing a plurality of methods in combination may be used.

As shown in FIG. 23, the dissecting instrument 3 in a state where it is attached to the blood vessel supporting instrument 2E, is arranged substantially in parallel to the arm portions 21a and 21b. By positioning the dissecting instrument 3 as described above with respect to the blood vessel supporting instrument 2E, the cutter blade 33 thereof is positioned between the needle portions 22a and 22b.

With this construction, the cutter blade 33 is movable in the direction substantially vertical to the longitudinal direction of the needle portions 22a and 22b. The cutter blade 33 in the first position (the state shown in FIG. 23) is positioned slightly closer to the proximal end (upward in FIG. 23) than the needle positions 22a and 22b and when it is displaced to the second position, it is inserted between the needle portions 22a and 22b.

Hereinafter, the use method of the surgical instrument 1A in the method of the sixth embodiment will be illustrated in detail.

With the cutter blade 33 at the first position as described above, the operation of piercing the needle portions 22a and 22b into the first blood vessel 10 (similar operation to that described in [1] in the method according to the second embodiment) is performed. The cutter blade 33 when it is in the first position is located at a position retracted (remote) from the first blood vessel 10 supported by the needle portions 22a and 22b. As a result, the cutter blade 33 does not contact the first blood vessel 10 at the time of this operation.

The dissecting instrument 3 may be detached from the blood vessel supporting instrument 2E in advance prior to piercing the needle portions 22a and 22b into the first blood vessel 10 and after completion of the operation, the dissecting instrument 3 may be attached to the blood vessel supporting instrument 2E.

Next, the operation button 35 is pushed down and the rod 32 and the cutter blade 33 are moved in the direction toward the distal end (in the direction toward the blood vessel 10). This moves the cuter blade 33 to the second position to pierce the first blood vessel 10 in the manner as illustrated in FIG. 12 to form the opening 102. In this case, as in the case of shown in FIG. 12, the first blood vessel 10 is formed of the opening 102 of approximately the same length as the width L2 of the cutter blade 33.

Since the range in which the piston 34 can move is controlled to a predetermined length by the cylinder 31, the amount of movement of the cutter blade 33 is also controlled to a certain amount. This ensures formation of the opening 102 having suitable length in the first blood vessel 10.

After the formation of the opening 102, the dissecting instrument 3 is detached from the blood vessel supporting instrument 2E. Then, operations similar to that described in [3] to [6] in the method according to the second embodiment are performed to fix the first blood vessel 10 and the second blood vessel 20 by means of the fixing instrument 70.

As illustrated above, the surgical instrument 1A exhibits similar actions and effects as those of the blood vessel supporting instrument 2C for use in the method according to the third embodiment. At the same time, it has the dissecting instrument 3 and hence the opening 102 can be formed in the first blood vessel 10. Since relative positional relationship between the distal end portion (cutter blade 33) of the dissecting instrument 3 and the needle portions 22a and 22b can be controlled, the opening 102 having a suitable size can be readily, quickly and securely formed in the first blood vessel 10 at an accurate position thereof.

<Seventh Embodiment>

Figure 25:
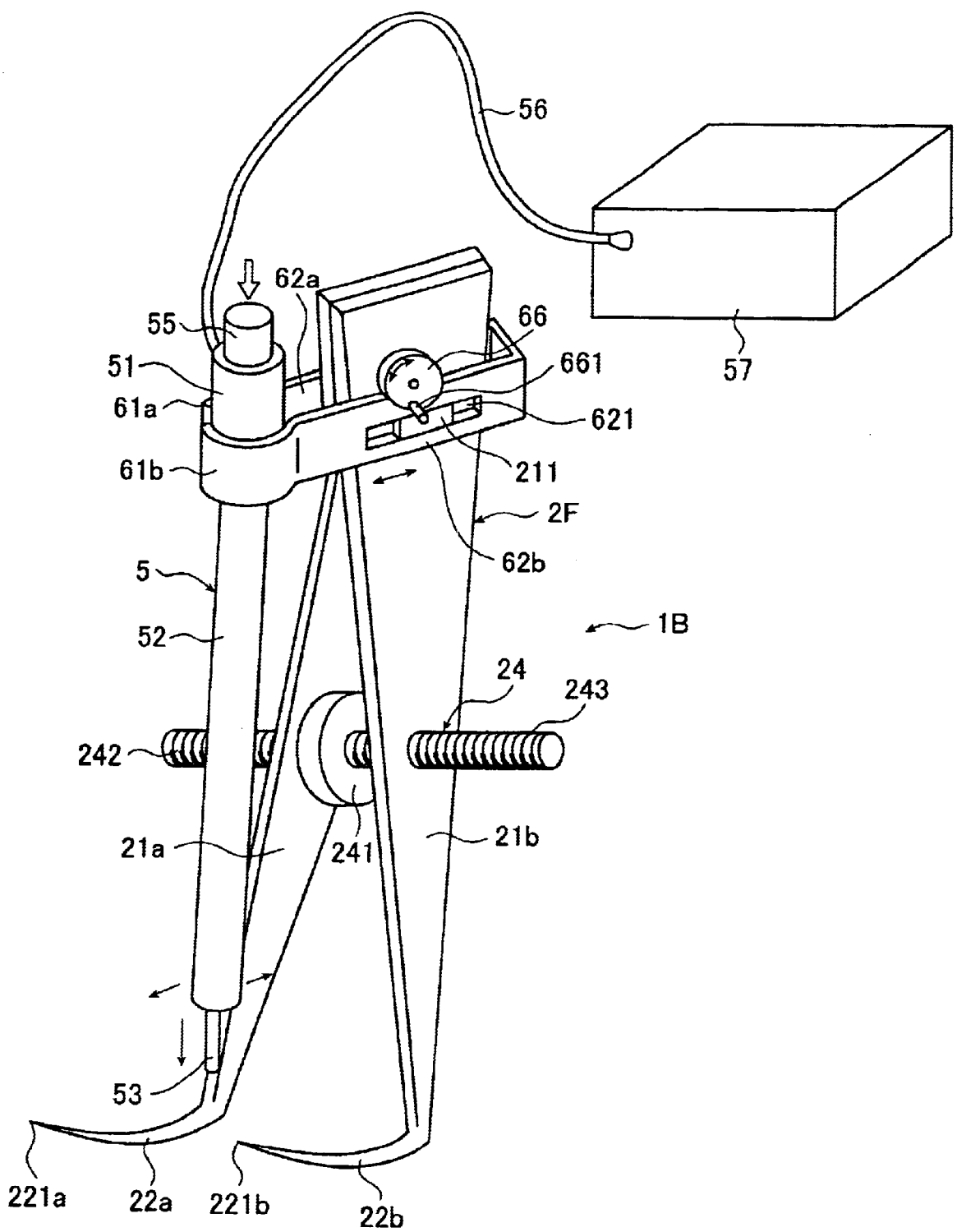
FIG. 25 is a perspective view showing a surgical instrument that comprises a blood vessel supporting instrument and a dissecting instrument, for use in the end-to-side blood vessel anastomosis method according to a seventh embodiment of the present invention.
Figure 26:
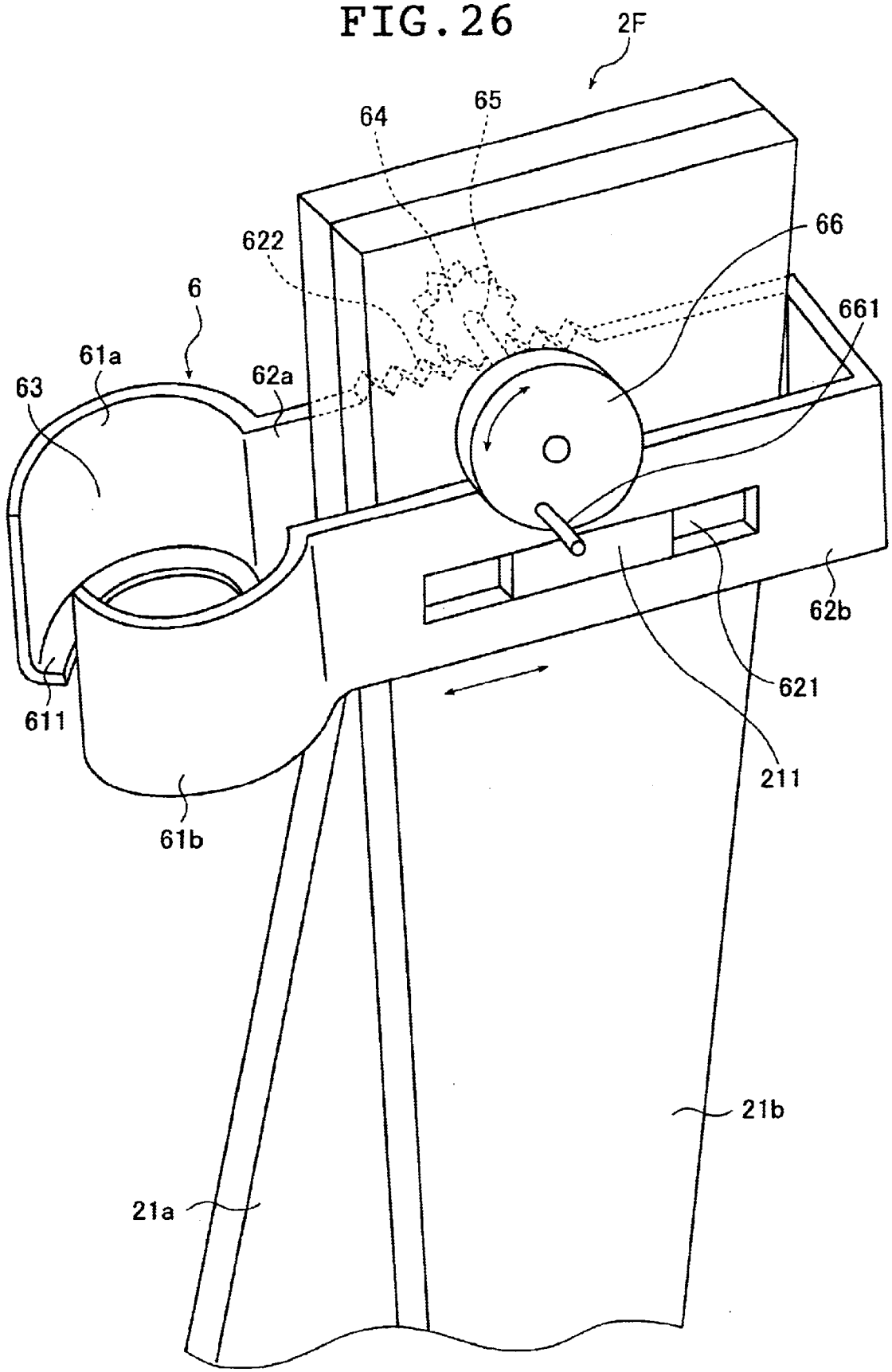
FIG. 26 is an enlarged perspective view showing a part of the surgical instrument on the proximal end side of the blood vessel supporting instrument shown in FIG. 25.

FIG. 25 is a perspective view showing a surgical instrument 1B that comprises a blood vessel supporting instrument and a dissecting instrument, for use in the end-to-side blood vessel anastomosis method according to a seventh embodiment of the present invention. FIG. 26 is an enlarged perspective view showing a part of the surgical instrument 1B shown in FIG. 25 on the proximal end side of the blood vessel supporting instrument 2F. In the following explanation, the upper side and lower side in FIGS. 25 and 26 are referred to as "proximal end" and "distal end", respectively. The direction toward the terminal ends of the needle portions 22a and 22b is referred to as "front" and the direction toward the roots of the needle portions 22a and 22b is referred to as "rear".

The method of the seventh embodiment is the same as the method of the sixth embodiment above except that a surgical instrument 1B shown in FIG. 25 is used instead of the surgical instrument 1A.

Hereinafter, the method of the seventh embodiment will be illustrated in detail with reference to FIGS. 25 and 26. The explanation will be centered on the differences from the method of the above-described embodiments and the explanation on the same or like matter will be omitted.

The blood vessel supporting instrument 2F used in the seventh embodiment is the same as the blood vessel supporting instrument 2E according to the fifth embodiment above except that the dissecting instrument attaching portion has a different construction from that of the dissecting instrument attaching portion of the blood vessel supporting instrument 2E. The surgical instrument 1B used in the present embodiment comprises the blood vessel supporting instrument 2F and the dissecting instrument 5 that can be attached to the blood vessel supporting instrument 2F.

The dissecting instrument 5 shown in FIG. 25 comprises an electric cautery or knife. It has a cylinder 51, a rod 52, a cutter blade portion 53 arranged at the distal end of the rod 52, and an operation button (operation portion) 55. The dissecting instrument 5 is electrically connected to an electric knife device 57 through a lead wire 56.

The rod 52 is arranged movable with respect to the cylinder 51 in a similar mechanism to that of the dissecting instrument 3 used in the sixth embodiment above. By pushing down the operation button 55, it can be moved in the direction toward the distal end thereof. With this construction, the cutter blade portion 53 can be displaced between a first position and a second position. In the first position, the cutter blade portion 53 is retracted from the first blood vessel 10 supported by the needle portions 22a and 22b in a manner similar to that of the dissecting instrument 3 used in the sixth embodiment (the state shown in FIG. 25). The cutter blade portion 53 is moved from the first position in the direction toward the distal end thereof to the second position, where the first blood vessel 10 is dissected. In a similar mechanism to that of the dissecting instrument 3 used in the sixth embodiment above, the cutter blade portion 53 can be maintained as positioned at the second position.

The blood vessel supporting instrument 2F has a dissecting instrument attaching portion 6, to which the dissecting instrument 5 can be attached. The dissecting instrument 5 in the state where it is attached to the blood vessel supporting instrument 2F is arranged substantially in parallel to the arm portions 21a and 21b. The cutter blade portion 53 is positioned between (or above) the needle portions 22a and 22b.

As shown in FIG. 26, the dissecting instrument attaching portion 6 comprises a pair of holding portions 61a and 61b that hold the distal end side of the cylinder 51 of the dissecting instrument 5 on both sides thereof, and supporting portions 62a and 62b that support the both holding portions 61a and 61b, respectively.

The holding portions 61a and 61b are arranged at the front ends of the supporting portions 62a and 62b, respectively. The holding portions 61a and 61b are each curved and arranged such that the inside portions of the curves oppose to each other. This forms a gap 63 having a form corresponding to the cylinder 51 between the both holding portions 61a and 61b.

The supporting portions 62a and 62b are each an elongate plate-shaped member. The supporting members 62a and 62b are arranged substantially in parallel to the needle portions 22a and 22b such that the supporting portions 62a and 62b clip the proximal end portions of the arm portions 21a and 21b. The rear ends of the supporting portions 62a and 62b are connected to each other.

When the distal end side of the cylinder 51 of the dissecting instrument 5 is inserted between the both holding portions 61a and 61b, the holding portions 61a and 61b hold (clip) the distal end side of the cylinder 51 because of the elasticity of the supporting portions 62a and 62b.

Flanges 611 that project inwardly are formed at the distal end portions of the holding portions 61a and 61b, respectively. By abutting the distal end of the cylinder 51 against the upper surface of the flanges 611, the dissecting instrument 5 can be attached to the blood vessel supporting instrument 2F with positioning it.

It is noted that the structure for attaching the dissecting instrument 5 to the dissecting instrument attaching portion 6 is not limited to the one described above but not to mention that it may be replaced by those utilizing various other methods in the same manner as the method according to the sixth embodiment above.

The supporting portions 62a and 62b are provided with rectangular elongate holes or slots 621, respectively, along the longitudinal direction. Rectangular parallelepiped protrusions 211 arranged at the arm portions 21a and 21b are inserted inside the holes 621, respectively. That is, the protrusions 211 and the slots 621 are movable relative to each other along the longitudinal direction of the slots 621. With this construction, the dissecting instrument attaching portion 6 is movable in the direction substantially parallel to the needle portions 22a and 22b. Therefore, the cutter blade portion (distal end portion) 53 of the dissecting instrument 5 attached to the dissecting instrument attaching portion 6 is also movable in the direction substantially parallel to the longitudinal direction of the needle portions 22a and 22b.

Above the supporting portion 62a, a pinion 64 is arranged and at the proximal end portion of the supporting portion 62a, a rack 622 is formed that can intermesh with the pinion 64.

The pinion 64 is fixed to one end portion of a shaft 65 arranged so as to penetrate through the hole portions formed in the arm portions 21a and 21b. An operation handle (operation portion) 66 is fixed to the other end portion of the shaft 65.

The operation handle 66 is provided with a knob 661. By touching the knob 661 with the fingers to rotate the operation handle 66, the rotational movement is translated into linear movement through the pinion 64 and the rack 622 to move the dissecting instrument attaching portion 6. That is, handling the operation handle 66 can move the cutter blade portion 53 of the dissecting instrument 5 in the direction substantially parallel to the longitudinal direction of the needle portions 22a and 22b.

The rotation angle of the operation handle 66 or the amount of the movement of the cutter blade portion 53 of dissecting instrument 5 can be obtained, for example, by providing the operation handle 66 with an indicator and attaching calibration to the circumference of the operation handle 66. This operation can facilitate the adjustment of the distance of movement of the cutter blade portion 53 of the dissecting instrument 5 so that an opening having a desired length can be readily formed in the blood vessel 10.

Hereinafter, the use of the surgical instrument 1B in the method according to the seventh embodiment will be illustrated in detail.

With the cutter blade portion 53 at the first position as described above, the operation of piercing the first blood vessel 10 with the needle portions 22a and 22b (similar operation to that of being described in [1] in the method according to the second embodiment) is performed. The cutter blade portion 53, when it is in the first position, is located at a position retracted (remote) from the first blood vessel 10 supported by the needle portions 22a and 22b. As a result, the cutter blade portion 53 does not contact the first blood vessel 10 at the time of this operation.

The dissecting instrument 5 may be detached from the blood vessel supporting instrument 2F in advance prior to piercing the first blood vessel 10 with the needle portions 22a and 22b and after completion of the piecing operation the dissecting instrument 5 may be attached to the blood vessel supporting instrument 2F.

Next, the operation button 55 is pressed and the rod 52 and the cutter blade portion 53 are moved in the direction toward the distal end (in the direction toward the blood vessel 10). The cutter blade portion 53 is therefore at the second position to contact the first blood vessel 10. Then, the cutter blade portion 53 can maintain the state where it is at the second position as described above. As a result, the cutter blade portion 53, which is at a high temperature due to high frequency current from the electric knife device 57, starts dissection of the first blood vessel 10.

Next, rotation of the operation handle 66 moves the cutter blade portion 53 in the direction substantially parallel to the longitudinal direction of the needle portions 22a and 22b. This moves the cutter blade portion 53 in the longitudinal direction of the first blood vessel 10 while contacting it. As a result, an opening 102 is formed in the first blood vessel 10. On this occasion, the opening 102 of a desired size can be formed by controlling the amount of rotation of the operation handle 66.

After the formation of the opening 102, the dissecting instrument 5 is detached from the blood vessel supporting instrument 2F. Then operations similar to that being described in [3] to [6] in the method according to the second embodiment are performed to fix the first blood vessel 10 and the second blood vessel 20 to each other by means of the fixing instrument 70.

As illustrated above, the surgical instrument 1B exhibits similar actions and effects as those of the blood vessel supporting instrument 2C for use in the method according to the fourth embodiment. At the same time, it has the dissecting instrument 5 and hence the dissection opening 102 can be formed in the first blood vessel 10. Since relative positional relationship between the distal end portion (cutter blade portion 53) of the dissecting instrument 5 and the needle portions 22a and 22b can be controlled, the opening 102 having a suitable size can be readily, quickly and securely formed in the first blood vessel 10 at an accurate position thereof.

Although explanation has been made on the case where the dissecting instrument 5 used is an electric knife, it may be also an ordinary knife with a blade, a supersonic knife or a laser probe (laser knife).

In the case where the dissecting instrument 5 is an ordinary knife, the dissection is carried out as illustrated in FIG. 12.

Figure 27:
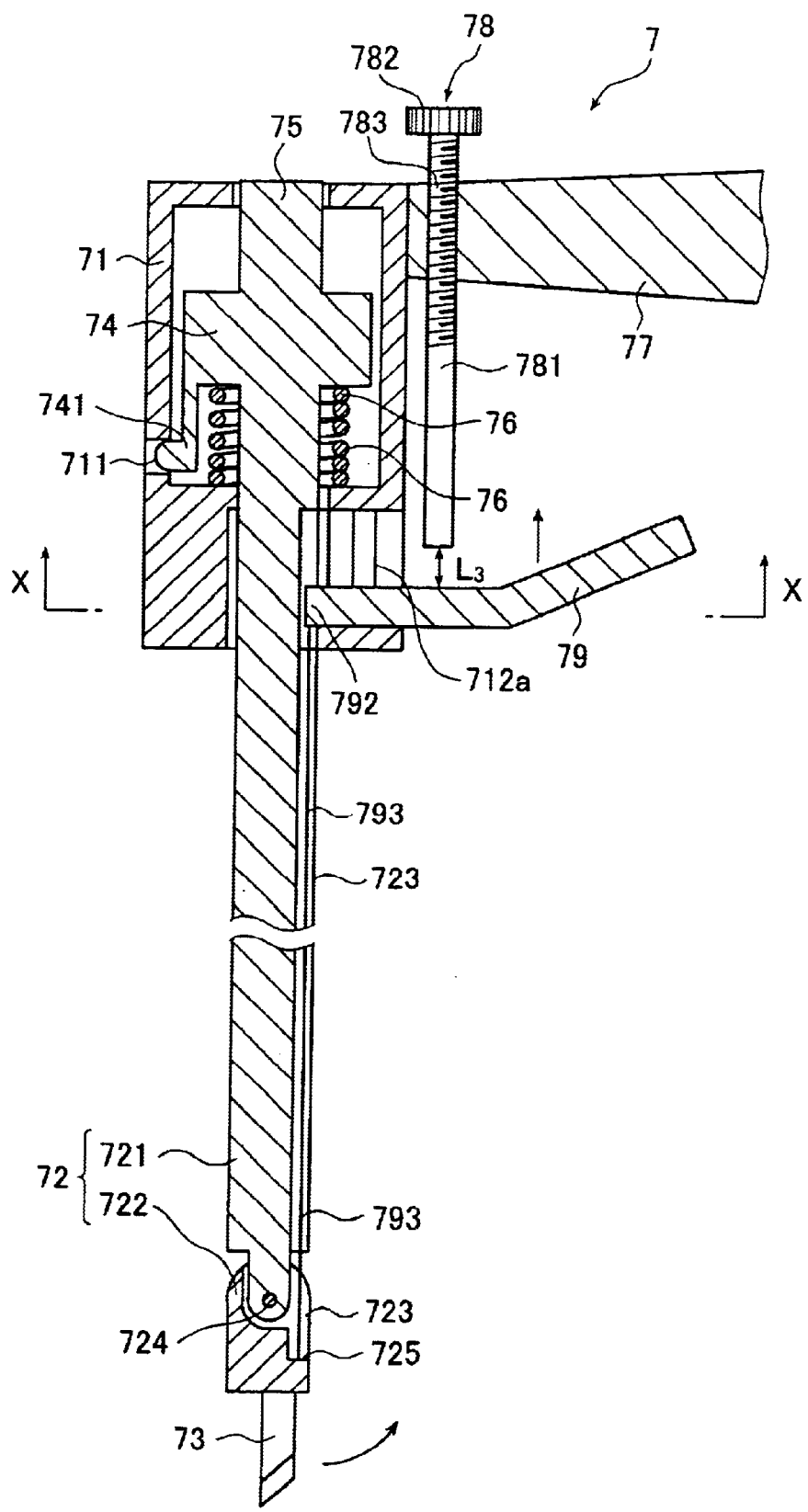
FIG. 27 is a vertical sectional view showing another example of structure of a dissecting instrument.
Figure 28:
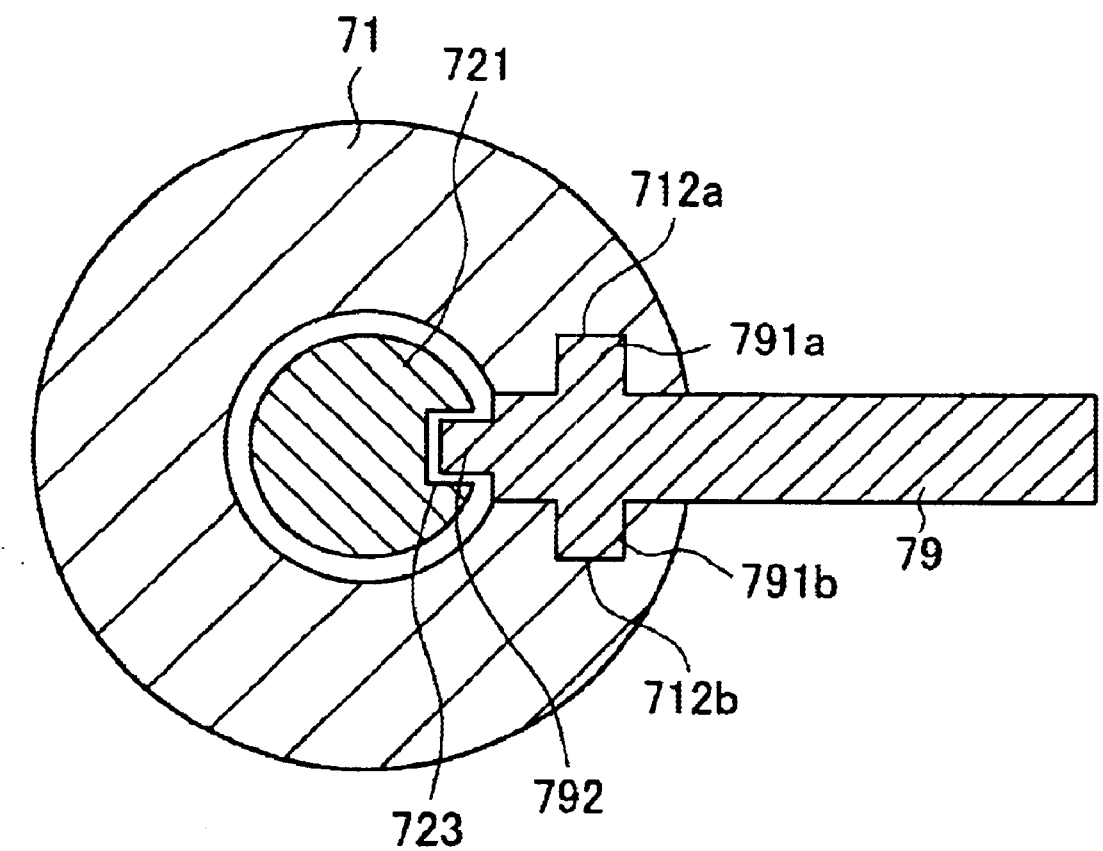
FIG. 28 is a transverse cross sectional view of the dissecting instrument taken along the line X—X in FIG. 27.

FIG. 27 is a cross sectional view showing an another structural example of a dissecting instrument. FIG. 28 is a transverse cross sectional view of the dissecting instrument shown in FIG. 27 cut along the line X—X. In the following explanation, the upper side and lower side in FIG. 27 are referred to as "proximal end" and "distal end", respectively.

The dissecting instrument 7 shown in FIGS. 27 and 28 can be used to be attached to the blood vessel supporting instrument 2E in the sixth embodiment above or the blood vessel supporting instrument 2F in the seventh embodiment above.

The dissecting instrument 7 comprises a cylinder 71, a rod 72 coaxially arranged to the cylinder 71, a cutter blade 73 arranged to the proximal end portion, a piston 74 slidably arranged inside the cylinder 71, an operation button 75 arranged at the proximal end portion of the piston 74, a coil spring 76 urging the piston 74 in the direction toward the proximal end, a protruding portion 77 protruding substantially vertically from the side of the cylinder 71 in the axial direction thereof, a stopper 78 arranged to the protruding portion 77, and a lever (handling portion) 79 provided so as to protrude from the cylinder 71 substantially in the same direction as that of the protrusion portion 77.

The rod 72, piston 74, operation button 75 and coil spring 76 are arranged to the cylinder 71 in the same manner as the dissecting instrument 3 in the sixth embodiment. That is, the rod 72 is movable with respect to the cylinder 71 in the axial direction thereof. In a position where the rod 72 moved a certain distance toward the distal end, an engaging piece 741 attached to the piston 74 is engaged with a hole 711 formed in the cylinder 71 to maintain the position of the rod 72 (the state shown in FIG. 27).

As a result, the cutter blade 73 attached to the distal end of the rod 72 is movable to a first position where it is retracted from the first blood vessel 10 and to a second position to dissect the first blood vessel 10 in the same manner as in the case of the dissecting instrument 3 in the sixth embodiment above. Engagement of the engaging piece 741 with the hole 711 can maintain the state where it is positioned at the second position.

The cylinder 71 is formed as extending in the direction toward the distal end further than the cylinder 31 of the dissecting instrument 3 in the sixth embodiment above. The extended portion is provided with the lever 79 movable along the axial direction of the cylinder 71. As shown in FIG. 28, a pair of protruding portions 791a and 791b formed in both sides of lever 79 are arranged such that they are inserted in a pair of guide grooves 712a and 712b formed in the cylinder 71, respectively. This construction makes the lever 79 movable along the axial direction of the cylinder 71.

A wire connecting portion 792 is provided as protruding from a root portion of the lever 79. The wire connecting portion 792 is inserted in a wire holding groove 723 formed along the outer periphery of the rod 72 in the longitudinal direction thereof.

The rod 72 comprises a rod body 721, a rotary portion 722 connected to the distal end of the rod body 721. The rod body 721 and the rotary portion 722 are connected to each other by a pin 724, for example. Thus, the rotary portion 722 is pivotal around the rod body 721. The cutter blade 73 is attached to the rotary portion 722 and pivots together with the rotary portion 722 so that it is movable with respect to the needle portions 22a and 22b.

The rotary portion 722 takes a position such that it is upright to the rod body 721 in the natural state due to the elastic force of a spring (not shown).

The wire holding groove 723 is formed continuously from the rod body 721 to the rotary portion 722. The rotary portion 722 is provided with a distal end wall 725 of the wire holding groove 723.

The wire connecting portion 792 of the lever 79 and the distal end wall 725 of the wire holding groove 723 are connected through a wire 793. The wire 793 is inserted and held in the wire holding groove 723. With this construction, movement of the lever 79 in the direction toward the proximal end of the cylinder 71 draws the wire 793 to rotate the rotary portion 722 against a force urged by a spring (not shown) so that the cutter blade 73 can move with respect to the needle portions 22a and 22b.

The protruding portion 77, as well as the lever 79, is a portion that is gripped by the hand of an operator when the lever 79 is operated and it projects from the proximal end portion of the cylinder 71 in the same direction as the lever 79.

On the root portion of the protruding portion 77, the stopper 78 that controls the range in which the lever 79 is movable is arranged substantially in parallel to the axial direction of the cylinder 71. The stopper 78 comprises a long shaft portion 781 and a knob 782 provided at a proximal end portion of the shaft portion. A thread portion 783 is formed on the proximal end side of the shaft portion 781. The site where the thread portion 783 is formed is intermeshed with the protruding portion 77.

When the knob 782 is turned by the hand the stopper 78 of this type moves along the cylinder 71 in the axial direction thereof, so that the distance between the distal end portion of the stopper 78 and the lever 79 (the length indicated by L3 in FIG. 27) can be varied. As a result, the movable range of the lever 79 can be adjusted. Along with this the angle of rotation of the rotary portion 722 can be adjusted. With this construction, turning the knob 782 to adjust the position of the stopper 78 allows the distance of the movement of the cutter blade 73 with respect to the needle portions 22a and 22b to be adjusted. As a result, the opening 102 having a desired size can be formed in the first blood vessel 10.

In the method according to the seventh embodiment, a surgical instrument comprising the dissecting instrument 7 and blood vessel supporting instrument as described above can be used by the following method.

First, the cutter blade 73 is placed in the first position as described above, and then the needle portions 22a and 22b are pierced into the first blood vessel 10.

Then, the operation button 75 is pushed down to place the cutter blade 73 in the second position. As a result, the distal end portion of the cutter blade 73 is in a state where it contacts or being pierced into the first blood vessel 10.

Then, the protruding portion 77 and the lever 79 are gripped by the hand and the lever 79 is moved in the direction toward the proximal end of the cylinder 71. This makes the cutter blade 73 to pivot around the pin 724, so that it dissects the first blood vessel 10 to form an opening 102 therein. In this instance, the position of stopper 78 is adjusted in advance.

As illustrated above, use of the surgical instrument having the dissecting instrument 7 allows the opening 102 having a suitable size to be readily, quickly and securely formed in an accurate position of the first blood vessel 10.

<Eighth Embodiment>

Figure 29:
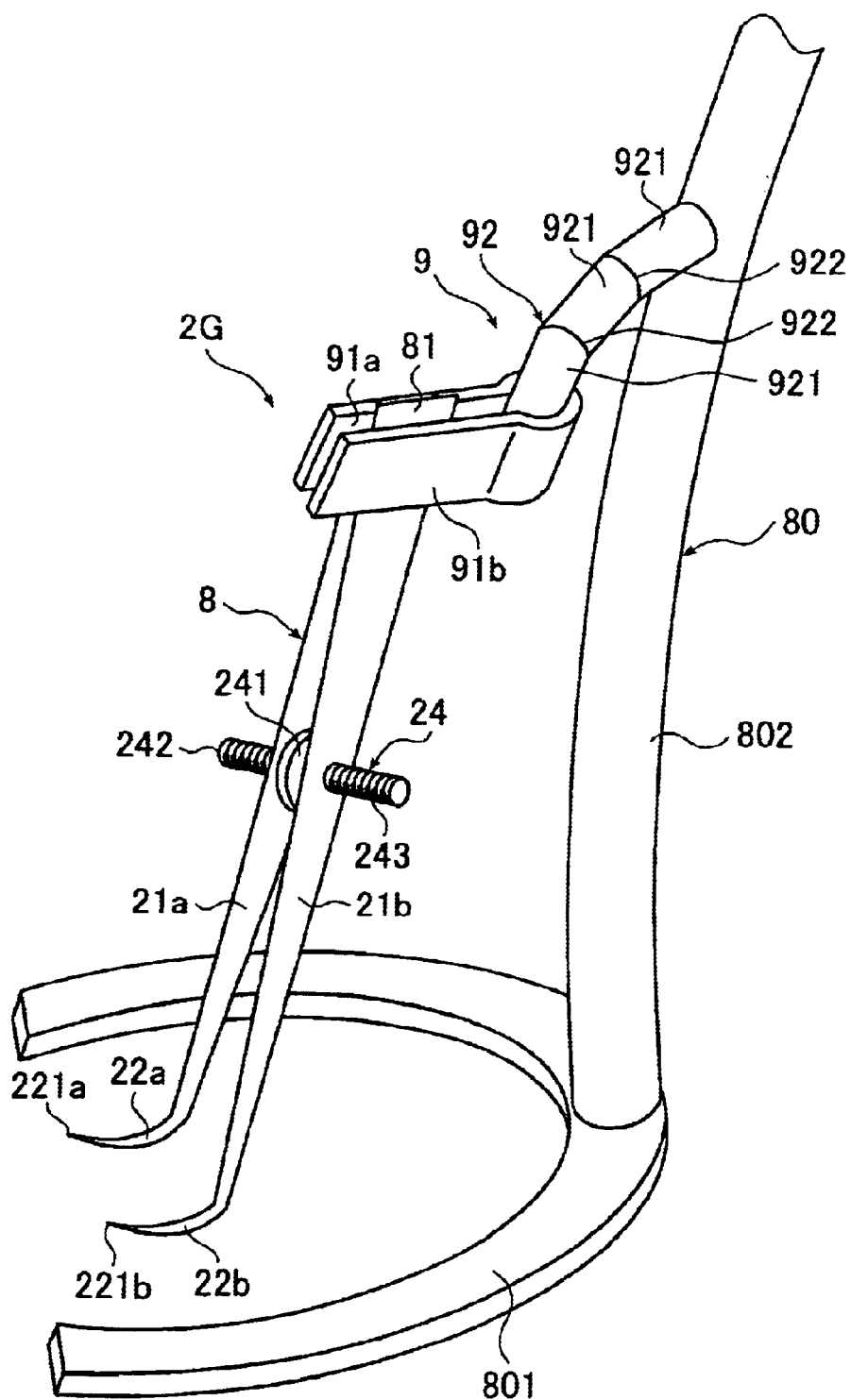
FIG. 29 is a perspective view showing a blood vessel supporting instrument for use in the end-to-side blood vessel anastomosis method according to an eighth embodiment of the present invention.

FIG. 29 is a perspective view showing a blood vessel supporting instrument for use in the end-to-side blood vessel anastomosis method according to an eighth embodiment of the present invention. In the following explanation, it is noted that the upper side and lower side in FIG. 29 are referred to as "proximal end" and "distal end", respectively. The direction toward the terminal ends of the needle portions 22a and 22b is referred to as "front" and the direction toward the roots of the needle portions 22a and 22b is referred to as "rear".

The method of the eighth embodiment is the same as the methods of the previous embodiments except that a blood vessel supporting instrument similar to the blood vessel supporting instrument 2C in the forth embodiment above is used as attached to a stabilizer that suppresses the movement the heart surface.

Hereinafter, the end-to-side blood vessel anastomosis method of the eighth embodiment of the present invention will be illustrated in detail with reference to FIG. 29. The explanation will be centered on the differences of the methods of the eighth embodiment from the methods of the previous embodiments and explanation on the same or like matter will be omitted.

The blood vessel supporting instrument 2G is the same as the blood vessel supporting instrument 2C in the fourth embodiment except that the instrument 2G is constructed so that it can be fixed (attached) to a stabilizer that suppresses the movement of the heart surface.

In the artery bypass graft (CABG) under heart beating, a stabilizer is used for suppressing the movement of the heart surface due to heart beating as much as possible to make the surgery operation easier. The stabilizer includes various types such as one that pushes the heart and one that absorbs the heart by vacuum suction (reduced pressure suction)

The blood vessel supporting instrument 2G used in the present embodiment is constructed so that it can be fixed (attached) to such a stabilizer and can more securely support blood vessels in a stabilized state.

A stabilizer 80 shown in FIG. 29 pushes the heart to suppress the movement of the heart surface and comprises a contact portion 801 that contacts a heart and a pole brace 802 for supporting the contact portion 801.

The contact portion 801 as a whole is in the form of a horseshoe (U-shaped). The pole brace 802 is provided as protruding substantially vertical to a plane including the contact portion 801 from a central portion in the longitudinal direction of the contact portion 801.

As shown in FIG. 29, the blood vessel supporting instrument 2G used in the present embodiment comprises a blood vessel supporting instrument body 8 and a fixing member 9 for fixing the blood vessel supporting instrument body 8 to the stabilizer 80.

The blood vessel supporting instrument body 8 is similar in construction to the blood supporting instrument 2C in the fourth embodiment above except that the blood vessel supporting instrument body 8 is provided with a contact portion 81 to be clipped by clipping portions 91a and 91b of the fixing member 9 on the proximal end portion of the arm portions 21a and 21b. The clipping portions 91a and 91b of the fixing member 9 will be explained hereinbelow.

The fixing member 9 comprises a pair of clipping portions 91a and 91b for clipping the proximal end portions of the arm portions 21a and 21b of the blood vessel supporting instrument body 8, a connection pipe 92 one end portion of which is fixed to the clipping portions 91a and 91b. The other end portion of the connection pipe 92 can be detachably fixed to the pole brace 802 of the stabilizer 80, for example, by means of threads. With this construction, the blood vessel supporting instrument body 8 and the stabilizer 80 can be fixed to each other through the fixing member 9.

The clipping portions 91a and 91b are elastic and the rear end portions thereof are fixed to each other. This allows the clipping portions 91a and 91b to clip (hold) the contact portion 81 of the blood vessel supporting instrument body 8 due to their elasticity.

The connection pipe 92 comprises a plurality of pipe members 921 joined (connected) to each other. Connecting portions 922 connecting the pipe members 921 to each other are flexible. With such construction, the blood vessel supporting instrument 2G can three-dimensionally adjust the positions of the needle portions 22a and 22b with respect to the stabilizer 80 (contact portion 801) for their positioning. As a result the needle portions 22a and 22b can be freely adjusted their position on a side portion of a blood vessel to be anastomosed and fixed thereto, so that the blood vessel can be supported in a more stable state and the anastomosis of a blood vessel can be further facilitated.

Here, the construction for fixing (connecting) the blood vessel supporting instrument body 8 to the fixing member 9 and the construction for fixing (connecting) the fixing member 9 to the stabilizer 80 may be various types. For example, those constructions utilizing fitting, screwing, absorption with a magnet or the like methods may be used. Also, constructions utilizing a plurality of methods in combination may be used. In place of the connection pipe 92, there may be used, for example, multi-jointed arm, bellows pipe and so forth.

Although the end-to-side blood vessel anastomosis method and instruments and devices used in the method according to the present invention are explained based on the embodiments illustrated in the appended drawings, the constructions of respective components of the instruments used in the present invention may be replaced by those having any desired constructions that can exhibit the same or similar functions.

For example, the blood vessel connecting instrument 1000 used in the first embodiment of the present invention comprises engaging members 1010, holding members 1020, a fastening member 1030, a pressing member 1040, a blood vessel supporting member 1050, and a receiving member 1060 as described above. However, it is sufficient for the blood vessel connecting instrument of the present invention to have at lest engaging members and holding members (holding means) of these components and all or a part of the other components may be omitted.

The each component may be used either in an integrated state or a connected state or as independent members. For example, the fastening members 1030 and a receiving member 1060 are parts that are used anew for every operation. Accordingly, they may be separate members independent of the body of the blood vessel connecting instrument 1000. As another construction, in the case where the second blood vessel is an artificial blood vessel, the receiving member 7 may be fixed or integrated to the second blood vessel in advance.

On the other hand, the blood vessel supporting instruments or surgical instruments used in the second to eighth embodiments may be, for example, those having 3 or more needle portions.

In the case where the distance between needle portions is variable, the distance may be increased or decreased in any desired direction.

In addition, the arm portions as a whole may have a bent or curved shape.

In the end-to-side blood vessel anastomosis method of the present invention, the first blood vessel and the second blood vessel are not limited to blood vessels from living body but may be artificial blood vessels.

Further, in the same manner as the end-to-side blood vessel anastomosis method of the present invention, a blood inlet port and/or a blood outlet port of a medical device having a passage for blood wherein can connect with a blood vessel that constitutes a part of a blood extracorporeal circulation circuit such as a pump-oxygenator, a dialyser, or a blood dialyzer may be connected to a linear opening provided by partially dissecting a side portion of a blood vessel extending in the longitudinal direction thereof.

The blood vessel supporting instruments, surgical instruments and blood connecting instrument of the present invention find wide range of application with respect to the type of blood vessel to be anastomosed. Using them, not only graft blood vessels such as great saphenous vein with both ends but also pedicle graft such as inner thoracic artery can be anastomosed with ease. Also, they may be applied to other end-to-side anastomosis method, end-to-end anastomosis method and side-to-side anastomosis method other than the end-to-side anastomosis methods in the above-mentioned embodiments.

Figure 30:
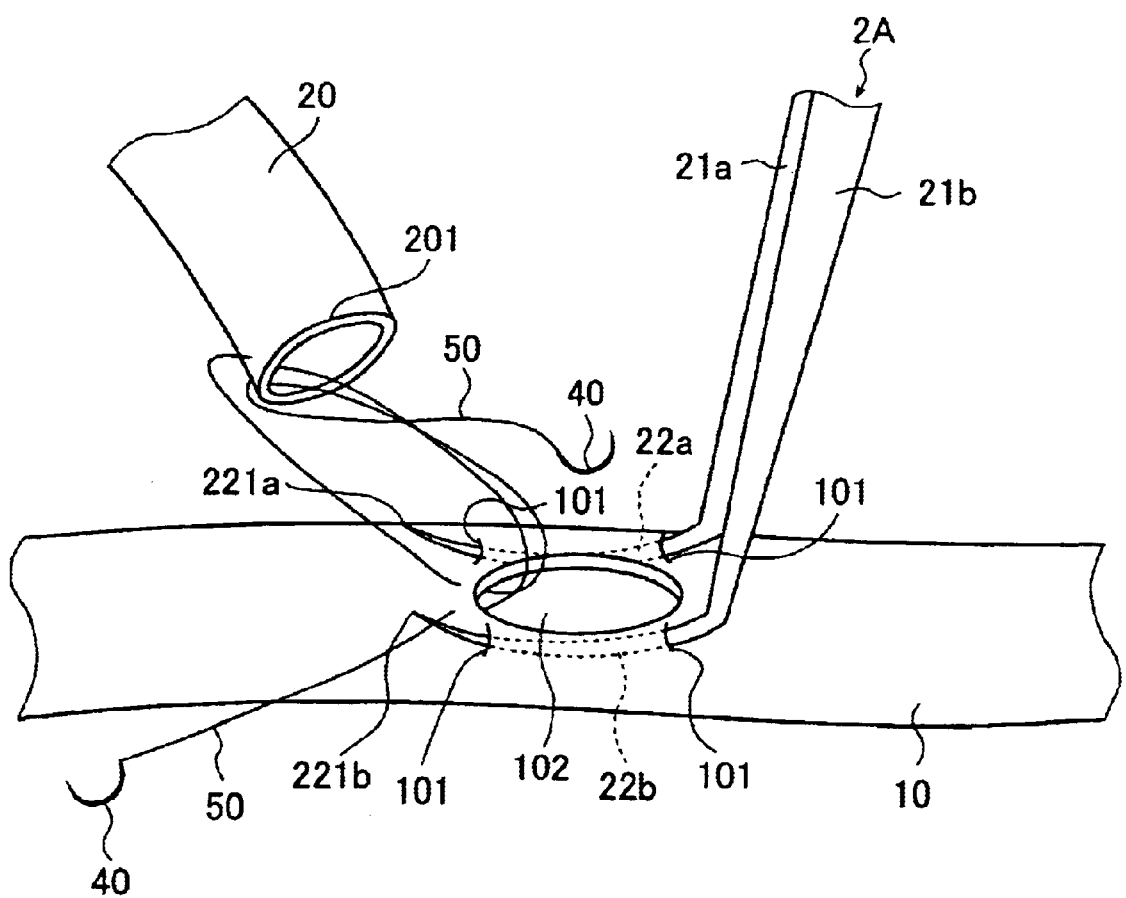

FIGS. 30 and 31 are schematic perspective views each showing other modes of utilization of the blood vessel supporting instrument 1A. In the method illustrated in FIGS. 30 and 31, after practicing the procedures [1] to [3] in the second embodiment of the present invention, the peripheral portion of the opening 102 in the first blood vessel 10 and the end portion 201 of the second blood vessel 20 are sutured to fix the blood vessels to each other.

As shown in FIG. 30, the peripheral portion of the opening 102 in the first blood vessel 10 and the end portion 201 of the second blood vessel 20 are alternately and repeatedly stitched by a suture needle 40 to pass a suture thread 50 through the peripheral portion of the opening 102 in the first blood vessel 10 and the end portion 201 of the second blood vessel 20.

Here, the circumference of the opening 102 in the first blood vessel 10 is supported by the blood vessel supporting instrument A and in a stable state so that the suture needle 40 can be readily pierced through the first blood vessel 10.

Because the opening 102 is expanded, the suture needle 40 can be introduced into or withdrawn from the opening 102 with ease, so that the operation of stitching the suture needle 40 through the peripheral portion of the opening 102 can be performed with ease.

Because the peripheral portion of the opening 102 in the first blood vessel 10 and the end portion 201 of the second blood vessel 20 are stitched around the entire periphery thereof, it is sometimes difficult to stitch the portion opposite to the side of the operator. Also in such case, by changing the direction of the needle portions 22a and 22b, the portion difficult to stitch can be directed to the side of the operator so that it can be placed in a state where stitching can be readily performed.

Then, the suture thread 50 is stressed and if necessary the suture thread is tied on. As a result, the end portion 201 of the second blood vessel 20 is connected to the opening of the first blood vessel 10 as shown in FIG. 31, thus completing the suturing.

Then, removing the needle portions 22a and 22b from the first blood vessel 10 concludes the anastomosis. The holes 101 through which the needle portions 22a and 22b are pierced are hold as small as possible as described above so that the wounds are immediately occluded due to the elasticity of the first blood vessel 10.

As explained above, according to the present invention, connection (anastomosis) of blood vessels to each other can be realized readily, securely and quickly so that loads on patients can be reduced.

In particular, in the case of connection of blood vessels of small diameters, work under narrow field of vision, works under hear beating and so forth, that have been conventionally difficult, quick and accurate connection of blood vessels is possible according to the present invention.

Furthermore, according to the present invention, the site on the inner surface of the blood vessel where the engaging portion is engaged is not exposed to blood flow. In addition, after the anastomosis, no foreign matter is present in the portion that contacts blood, so that there is little fear that thrombin formation can occur.

Furthermore, because remote manipulation is possible as well as the operation is easy, the present invention can be applied to, for example, operation of performing blood vessel connection of heart without thoracotomy (operation under an endoscopy). Therefore, the present invention finds a wide range of application.

What is claimed is:

1. A method of end-to-side anastomosis of blood vessels for connecting a side portion of a first blood vessel to an end portion of a second blood vessel, comprising:

holding a first site on the side portion of the first blood vessel located in the vicinity of a peripheral portion of an opening formed on the side portion of the first blood vessel using a holder, and partially elevating the side portion of the first blood vessel;

superimposing a second site on the side portion of the first blood vessel on the end of the second blood vessel and fixing them to each other with a ring-shaped fixing member, the second site being more distant from the peripheral portion of the opening formed on the side portion of the first blood vessel than the first site; and detaching the holder from the first blood vessel when the first and second blood vessels are fixed by the fixing member or after they are fixed.

2. A blood vessel connecting instrument according to claim 1, wherein the holding means is a holding member having a clipping portion that can clip a part of the first blood vessel in the vicinity of a peripheral portion of the opening in the first blood vessel between it and the engaging portion.

3. A method of end-to-side anastomosis of blood vessels according to claim 1, wherein a blood vessel connecting instrument is utilized, the blood vessel connecting instrument comprising:

at least one engaging member having an engaging portion for enabling engagement in the vicinity of the peripheral portion of the opening formed on the first blood vessel from inside thereof;

holding means for holding the state of engagement of the engaging portion in the vicinity of the peripheral portion of the opening in the first blood vessel;

a fastener member for superimposing a portion in the vicinity of the peripheral portion of the opening in the first blood vessel on the end portion of the second blood vessel and fastening them to fix them to one another, wherein with respect to the peripheral portion of the opening in the first blood vessel, a fixing position where the first blood vessel and the second blood vessel are fixed with the fastening member is more remote than a position where the engaging portion is engaged with the inner surface of the first blood vessel.

4. A method of end-to-side anastomosis of blood vessels according to claim 1, wherein a blood vessel supporting instrument is utilized, the blood vessel supporting instrument comprising:

a pair of arm portions and a pair of needle portions attach to an end portion of the both arm portions and arranged substantially parallel to each other.

the needle portions being pierced into the blood vessel to support and manipulate a portion of the blood vessel.

5. A blood vessel connecting instrument for connecting a second blood vessel to a side portion of a first blood vessel, comprising:

at least one engaging member having an engaging portion for enabling engagement in the vicinity of a peripheral portion of an opening formed on the first blood vessel from inside thereof:

holding means for holding the state of engagement of the engaging portion in the vicinity of the peripheral portion of the opening in the first blood vessel;

a fastener member for superimposing a portion in the vicinity of the peripheral portion of the opening in the first blood vessel on the end portion of the second blood vessel and fastening them to fix them to one another, wherein with respect to the peripheral portion of the opening in the first blood vessel, a fixing position where the first blood vessel and the second blood vessel are fixed with the fastening member is more remote than a position where the engaging portion is engaged with the inner surface of the first blood vessel.

6. A blood vessel connecting instrument according to claim 5, the engaging member is arranged in the holding member and is movable in a longitudinal direction thereof.

7. A blood vessel connecting instrument according to claim 5, comprising a plurality of engaging members, the distance between at least two of the engaging members being variable.

8. A blood vessel connecting instrument according to claim 5, wherein the engaging member comprises a linear body and the engaging portion comprises a bent end portion of the linear body.

9. A blood vessel connecting instrument according to claim 5, wherein the fastener member is ring-shaped and the diameter thereof is variable.

10. A blood vessel connecting instrument according to claim 5, further comprising a guide portion for guiding the fastener member to the fixing position of the first blood vessel and the second blood vessel, and a moving means for moving the fastener member to the fixing position.

11. A blood vessel connecting instrument according to claim 5, wherein the fastener member has a receiving member for receiving fastening force of the fastener member.

12. A blood vessel connecting instrument according to claim 11, wherein the receiving member is ring-shaped.

13. A blood vessel connecting instrument according to claim 12, wherein the receiving member has a groove on its outer periphery.

14. A blood vessel connecting instrument according to claim 11, further comprising a blood vessel support member for supporting the second blood vessel together with the receiving member.

15. A blood vessel connecting instrument according to claim 14, wherein the blood vessel support member has a pair of arm portions that can come closer to and remoter from each other.

* * * * *

UNITED STATES PATENT AND TRADEMARK OFFICE
CERTIFICATE OF CORRECTION

PATENT NO. : 6,746,459 B2
DATED : June 8, 2004
INVENTOR(S) : Yukitoshi Kato

It is certified that error appears in the above-identified patent and that said Letters Patent is hereby corrected as shown below:

Column 29,
Line 45, change "claim 1" to -- claim 5 --.

Column 30,
Line 33, add -- wherein -- after "claim 5".

Signed and Sealed this

Second Day of May, 2006

JON W. DUDAS
*Director of the United States Patent and Trademark Office*